(12) United States Patent  
Khismatullin et al.

(10) Patent No.: US 11,333,656 B2  
(45) Date of Patent: May 17, 2022

(54) APPARATUS, SYSTEMS AND METHODS FOR NON-CONTACT RHEOLOGICAL MEASUREMENTS OF BIOLOGICAL MATERIALS

(71) Applicants: Trustees of Boston University, Boston, MA (US); The Administrators of the Tulane Educational Fund, New Orleans, LA (US)

(72) Inventors: Damir Khismatullin, Metairie, LA (US); Ray Holt, Framingham, MA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 15/068,126

(22) PCT Filed: Sep. 15, 2014

(86) PCT No.: PCT/US2014/055559  
§ 371 (c)(1),  
(2) Date: Mar. 11, 2016

(87) PCT Pub. No.: WO2015/038998  
PCT Pub. Date: Mar. 19, 2015

(65) Prior Publication Data  
US 2017/0016878 A1 Jan. 19, 2017

Related U.S. Application Data

(60) Provisional application No. 61/877,662, filed on Sep. 13, 2013.

(51) Int. Cl.  
*G01N 33/49* (2006.01)  
*G01N 11/02* (2006.01)  
(Continued)

(52) U.S. Cl.  
CPC ........ *G01N 33/4905* (2013.01); *G01N 11/02* (2013.01); *G01N 11/16* (2013.01); *G01N 2011/0073* (2013.01)

(58) Field of Classification Search  
CPC .... G01N 33/4905; G01N 11/02; G01N 11/16; G01N 2011/0073  
(Continued)

(56) References Cited

U.S. PATENT DOCUMENTS

| 4,284,403 A * | 8/1981 | Rey | G10K 15/00 |
| | | | 181/0.5 |
| 4,759,775 A * | 7/1988 | Peterson | A61M 1/36 |
| | | | 210/188 |

(Continued)

FOREIGN PATENT DOCUMENTS

| DE | 2709698 | 9/1978 |
| DE | 2709698 A1 * | 9/1978 |
| WO | 2011035162 | 3/2011 |

OTHER PUBLICATIONS

Puskar et al., "Miniaturization for Chemistry, biology & bioengineering", Sep. 2007, pp. 1125-1130, vol. 7, Lab on a Chip.*

(Continued)

*Primary Examiner* — Marrit Eyassu  
(74) *Attorney, Agent, or Firm* — Dentons Davis Brown, P.C.; Matthew Warner-Blankenship

(57) ABSTRACT

An acoustical non-contact levitation system and method for eliciting the deformation response of biological samples, coupled with the data analysis to yield quantitative measures of established time-dependent viscoelastic material properties. Embodiments allow for measurement to occur in near-real-time by way of a computer. In use, a biological sample is placed in an acoustic levitator, where it is induced to oscillate, such that material properties of the sample can be (Continued)

observed and analyzed by way of a camera and/or photodiode.

16 Claims, 15 Drawing Sheets

(51) Int. Cl.
*G01N 11/16* (2006.01)
*G01N 11/00* (2006.01)

(58) Field of Classification Search
USPC .......................................................... 73/54.41
See application file for complete search history.

(56) References Cited

U.S. PATENT DOCUMENTS

| | | | | |
|---|---|---|---|---|
| 5,056,357 | A * | 10/1991 | Dymling | G01F 1/663 73/54.41 |
| 5,613,940 | A | 3/1997 | Ramano | |
| 6,029,518 | A * | 2/2000 | Oeftering | B01D 17/041 210/748.02 |
| 6,067,859 | A * | 5/2000 | Kas | G21K 1/006 250/251 |
| 6,925,856 | B1 * | 8/2005 | Williams | G01N 11/16 73/54.41 |
| 7,712,353 | B2 * | 5/2010 | Janssen | B01F 5/0695 366/110 |
| 8,385,997 | B2 * | 2/2013 | Hyde | A61B 5/14546 600/310 |
| 8,647,886 | B1 * | 2/2014 | Sacchetti | G01N 21/51 435/2 |
| 8,685,178 | B2 * | 4/2014 | Do | B01F 11/0258 148/239 |
| 2002/0016239 | A1 | 11/2002 | Kaduchak et al. | |
| 2003/0049642 | A1 * | 3/2003 | Nilsson | C30B 7/00 435/6.16 |
| 2003/0154790 | A1 * | 8/2003 | Venturelli | B29C 35/0805 73/570.5 |
| 2007/0086919 | A1 * | 4/2007 | Akcakir | G01Q 20/02 422/82.05 |
| 2007/0119714 | A1 * | 5/2007 | Schnelle | B01L 3/502761 204/547 |
| 2012/0244564 | A1 * | 9/2012 | Walker | G01N 29/4472 435/13 |

OTHER PUBLICATIONS

Zheng et al., 1998, The Study of Evaporation of Mulitcomponent Drops Using an Acousto-Electric Levitator, Yale Acoustics Laboratory, Yale University, New Haven, Conneticut 06520-8286, pp. 139-140.*

Alaa Omrane et al., Laser techniques in acoustically levitated micro droplets, Miniaturisation For Chemistry, Biology & Bioengineering, Apr. 2004.*

J. Gregory McDaniel et al., Measurement of aqueous foam rheology by acoustic levitation, Mar. 2000, The American Physical Society, vol. 61, No. 3, pp. R2204-R2207 (Year: 2000).*

Georgescu et al., "Design of a system to measure light scattering from individual cells excited by an acoustic wave", "Optics Express", Mar. 3, 2008, vol. 16, No. 6.

Ljiljana Puskar et al., "Miniaturisation for Chemistry,biology & bioengineering", Sep. 2007, pp. 1126-1127, vol. 7, No. Figures 1&2, Publisher: Lab on a Chip.

Georgescu et al., "Design of a system to measure light scattering from individual cells excited by an acoustic wave", "Optical Express", Mar. 17, 2008, pp. 3496-3503, vol. 16, No. 6, Publisher Optical Society of America.

McDaniel et al., "Measurement of aqueous foam rheology by acoustic levitation", "Rapid Communications, Physical Review E", Mar. 3, 2000, pp. R2204-R2207, vol. 61, No. 3, Publisher: The American Physical Society.

* cited by examiner

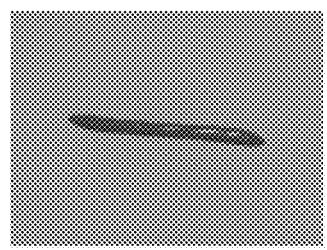 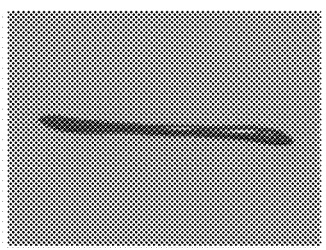 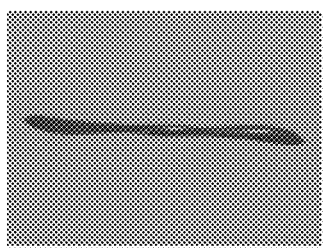
FIG. 5A  FIG. 5B  FIG. 5C
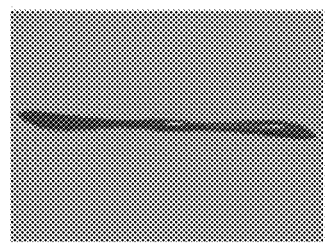 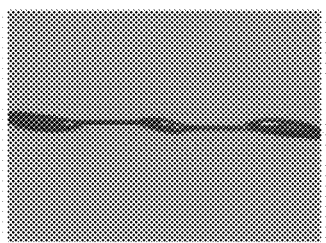 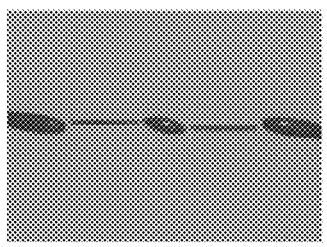
FIG. 5D  FIG. 5E  FIG. 5F
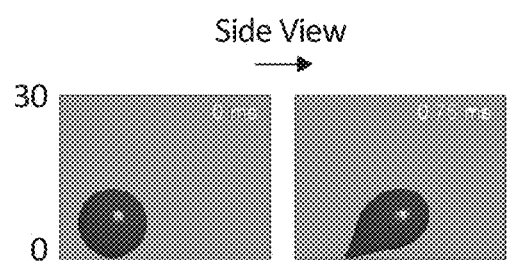 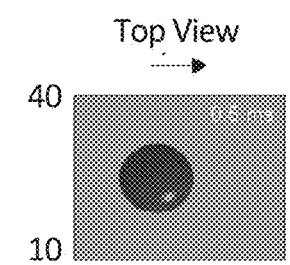 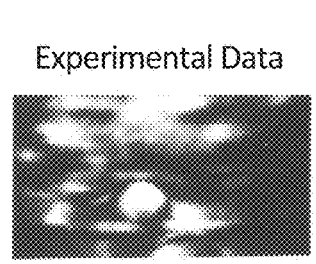
FIG. 5G  FIG. 5H  FIG. 5M  FIG. 5P
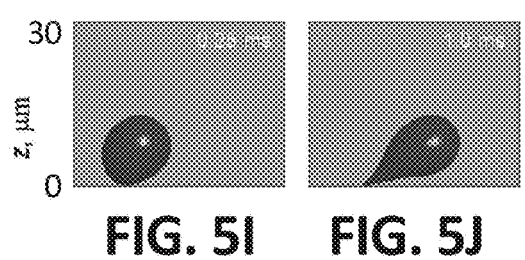 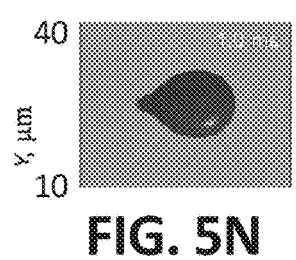 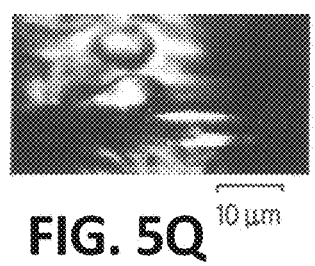
FIG. 5I  FIG. 5J  FIG. 5N  FIG. 5Q
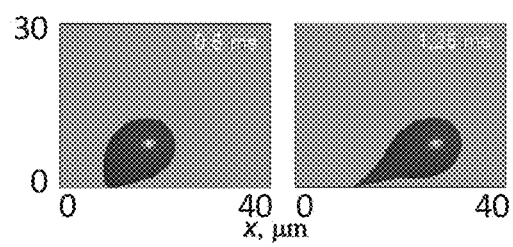 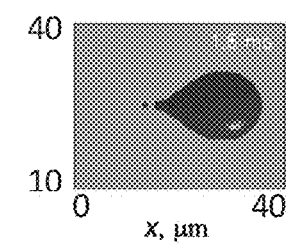
FIG. 5K  FIG. 5L  FIG. 5O X-view
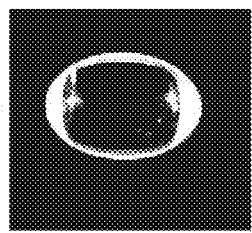
FIG. 12A
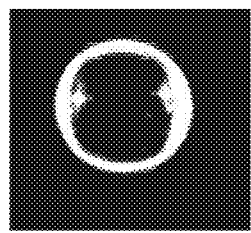
FIG. 12B
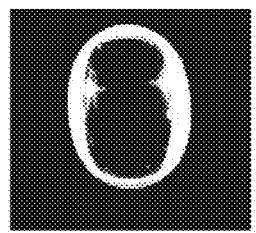
FIG. 12C
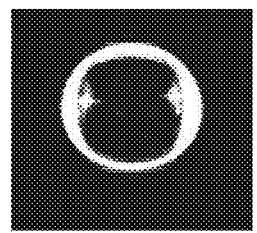
FIG. 12D
Z-view
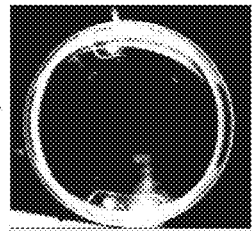
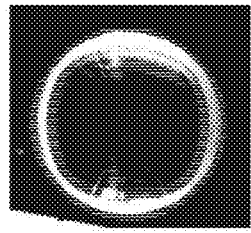
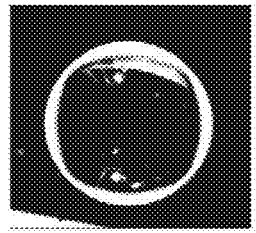
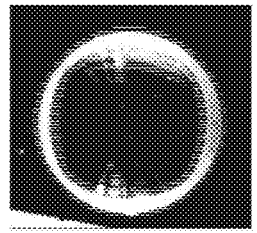
time(sec)  0.00    0.10    0.20    0.30
FIG. 12E   FIG. 12F   FIG. 12G   FIG. 12H

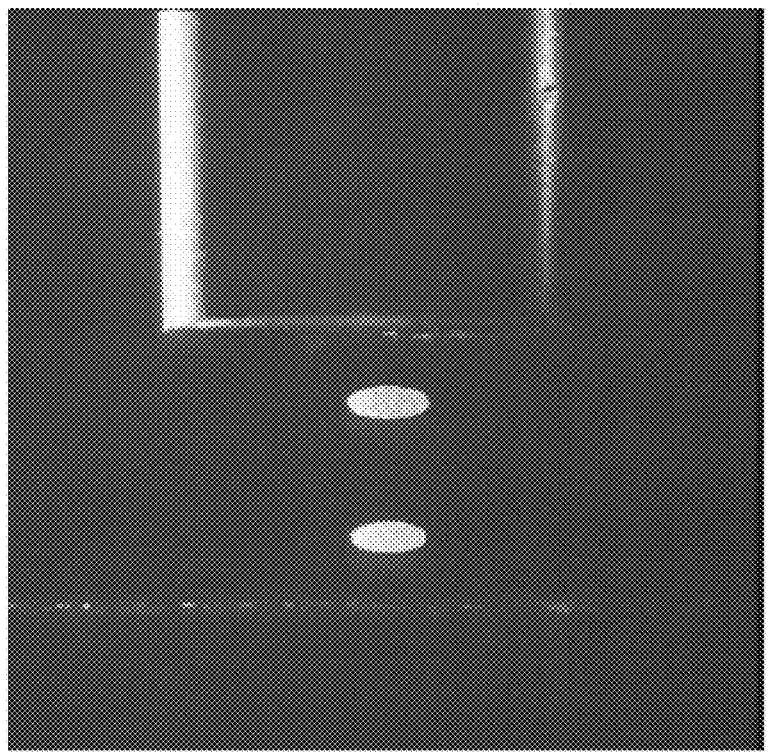
FIG. 14A
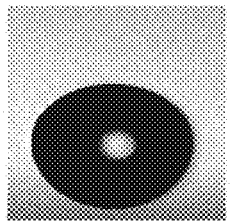 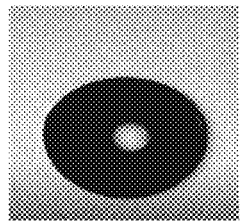 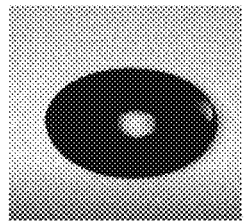 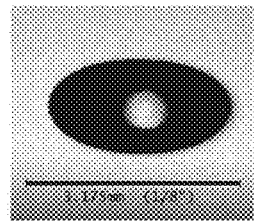
FIG. 14B　　FIG. 14C　　FIG. 14D　　FIG. 14E

APPARATUS, SYSTEMS AND METHODS FOR NON-CONTACT RHEOLOGICAL MEASUREMENTS OF BIOLOGICAL MATERIALS

CROSS-REFERENCE TO RELATED APPLICATION(S)

This application claims the benefit under 35 U.S.C. § 371 to International PCT Patent Application No. PCT/US 14/55559, filed on Sep. 15, 2014, which claims priority to U.S. Patent Application 61/877,662, filed Sep. 13, 2013, both of which are hereby incorporated herein in their entireties by this reference.

TECHNICAL FIELD

The disclosure relates to various systems, methods and apparatus for the measurement of certain properties of various fluids.

BACKGROUND

A blood clot or a thrombus is a clump of blood with fibrin, platelets, and other cellular elements. It is formed as a result of blood coagulation. Fibrin is a fibrous protein that forms the clot scaffold. It is made from fibrinogen, a soluble plasma glycoprotein, during the coagulation cascade. Clotting is essential for life because it prevents blood loss from the site of vessel injury (bleeding), but the formation of thrombi in intact vessels (thrombosis) leads to life-threatening conditions such as pulmonary embolism, stroke, or heart attack. A delicate balance of pro- and anti-coagulation factors in the circulating blood that prevents both excessive bleeding and thrombosis is often disturbed in patients undergoing surgery or during cardiovascular and liver disorders.

A blood clot and its major constituents, fibrin and blood cells, show viscoelastic behavior; i.e., they are characterized by at least two material constants, one (viscosity or loss modulus) describing their viscous properties and another (shear modulus, relaxation time, or storage modulus) describing their elastic properties. Most experimental studies on clot viscoelasticity were done with fibrinogen solutions but not with whole blood. The shear modulus and viscosity for various types of fibrin clots have been measured. It was found that clot viscoelastic properties critically depend on fibrin fiber thickness and the presence of a cross-linking protein (Factor XIIIa) and tetrapeptides Gly-Pro-Arg-Pro (GPRP) and Gly-His-Arg-Pro (GHRP) in the solution. Without cross-linking, clots with thin fibers ("fine clots"), made at high pH and high concentration of thrombin, were less viscous and elastic than clots with thick fibers ("coarse clots"). Another important result was that a linear viscoelastic model was a good approximation to describe unligated fibrin clots. Ligation with Factor XIIIa suppressed the creep (lowered the viscosity) of coarse clots to nearly zero and increased the clot stiffness (storage modulus), i.e., when cross-linked, fibrin clots behaved as a purely elastic material. Elasticity of an unligated clot decreased and its viscosity increased with concentration of the tetrapeptides GPRP and GHRP. At a critical concentration of 5.8 mM, the clot was liquefied. This occurs because GPRP and GHRP bind to a fibrin monomer and induce fibrin depolymerization in the absence of cross-linking proteins. Most of these studies were done by using a Plazek torsion pendulum. In this rheometric technique, a blood clot sample is located between two circular plates. One of the plates (upper plate) is connected to the torsion rod and can move under application of torque but another plate is held stationary. When the torsion arm of the apparatus is set into motion, the sample undergoes shear deformation. Its elastic and loss moduli can then be determined from the relationship between the imposed torque and the angular displacement of the upper plate (which is a function of time at constant torque). This is a contact method, in which its accuracy critically depends on how strong adhesion of the clot to the upper plate is. Other rheometric techniques used for measurement of fibrin clot viscoelasticity include a cone-and-plate rheometer, a free-floating gel device, and oscillatory flow instrument.

While certain novel features of this invention shown and described below are pointed out in the claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention. No feature of the invention is critical or essential unless it is expressly stated as being "critical" or "essential."

BRIEF SUMMARY

The present disclosure provides a novel device and methods for noncontact rheological measurement of biological materials in which the sample will be levitated in a host fluid by acoustic radiation forces.

In certain embodiments, the rheological measurement of blood samples, such as whole blood, is performed.

In some embodiments, the device and methods can provide near real time rheological measurements of fluids and tissues.

In some embodiments, sample sizes as small as 0.033 ml may be used in the disclosed device.

In some embodiments, the device and methods allow for noncontact measurement and thus no contact contamination or spurious nucleation of clotting cascade.

In some embodiments, the methods may be referred to as "acoustic tweezing rheometry." In some embodiments, the methods may be referred to as "acoustic tweezing thromboelastometry."

An advantage of this approach over optical tweezers, an optical method for noncontact manipulation, is that the acoustic wave energy absorbed by the sample is several orders less than that absorbed by laser irradiation. This minimizes deleterious effects of the external force field (such as heating) on blood and other coagulation or on changes in the polymerization dynamics of biological samples or reactive fluids.

In Example 1, a rheometry system for the rheological measurement of a biological sample comprises an acoustic levitator further comprising an acoustic reflector, a transducer, a light source, and a camera, and at least one function generator; and a data processing system comprising a computer in operational communication with the function generator and acoustic levitator, such that the acoustic levitator is configured to induce sample oscillation and the data processing system is configured to analyze the material properties of the biological sample by way of the induced sample oscillation.

In Example 2, the rheometry system of Example 1, wherein the transducer modulates the function generator.

In Example 3, the rheometry system in Example 1, wherein at least one function generator provides a carrier frequency.

In Example 4, the rheometry system of Example 3, wherein the function generator providing the carrier frequency provides a carrier frequency of at least 10 kHz.

In Example 5, the rheometry system of Example 1, further comprising a sample introduction device.

In Example 6, the rheometry system of Example 5, wherein the sample introduction device is a needle.

In Example 7, the rheometry system of Example 1, wherein at least one function generator provides amplitude modulation.

In Example 8, the rheometry system of Example 7, wherein the function generator providing amplitude modulation, modulates amplitude using step forcing.

In Example 9, the rheometry system of Example 8, wherein the acoustic pressure amplitude is increased or decreased with a rise time of 1 ms.

In Example 10, the rheometry system of Example 7, wherein the function generator providing amplitude modulation, modulates amplitude using swept-frequency sine forcing In Example 11, the rheometry system of Example 1, wherein the rheometry system is used to measure the rheological properties of whole blood.

In Example 12, the rheometry system of Example 1, wherein the rheometry system is used to measure the rheological properties of blood clots.

In Example 13, a rheometry system for the rheological measurement of a biological sample, the system comprising an acoustic levitator further comprising an acoustic reflector, a transducer; a light source; and a photodiode; and at least one function generator configured to generate a carrier wave; and a data processing system comprising a computer in operational communication with the function generator and acoustic levitator; wherein the acoustic levitator is configured to induce modulations in acoustic pressure and the data processing system is configured to analyze the material properties of the biological sample by way of the induced modulations.

In Example 14, the rheometry system of Example 13, further comprising a camera.

In Example 15, the rheometry system of Example 14, wherein the amplitude of carrier wave is modulated by a sine wave with frequency between 100 and 1,000 Hz.

In Example 16, the rheometry system of Example 15, wherein the function generator modulates amplitude using ramp forcing.

In Example 17, the rheometry system of Example 13, wherein the rheometry system is used to measure the rheological properties of whole blood.

In Example 18, the rheometry system of Example 13, wherein the rheometry system is used to measure the rheological properties of blood clots.

In Example 19, a method of measuring the rheological properties of biological materials, the method comprising transferring a biological sample into an acoustic levitator; modulating the amplitude of pressure within the acoustic levitator; taking measurements of the biological sample; and analyzing the measurements of the biological sample to determine the sample's rheological properties.

In Example 20, the method of Example 19, wherein the acoustic levitator further comprises an acoustic reflector; a transducer; a light source; a photodiode; a camera, at least one function generator configured to generate a carrier wave; and a data processing system comprising a computer in operational communication with the function generator and acoustic levitator.

While multiple embodiments are disclosed, still other embodiments of the disclosure will become apparent to those skilled in the art from the following detailed description, which shows and describes illustrative embodiments of the rheometry system, systems and methods. As will be realized, the rheometry system, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

FIGS. 5A-F depict photographs of a Newtonian drop in a viscoelastic matrix, according to an exemplary embodiment.

FIGS. 5G-L depict side view computed shapes over time of an adherent leukocyte, according to an exemplary embodiment.

FIGS. 5M-O depict top view computed shapes over time of an adherent leukocyte, according to the exemplary embodiment of FIGS. 5G-L.

FIGS. 5P-Q depict in vivo images of the embodiments of FIGS. 5G-O.

FIG. 12A-H are X- and Y-views of a cycle of the normal mode oscillation (n=2, or quadrupole mode) of a spheroidal sample one embodiment of an acoustic levitator over time.

FIG. 14A shows two samples simultaneously acoustically levitated and deformed in one embodiment of the system.

FIG. 14B-E show a sequence of increasingly deformed samples resulting from a linear ramp amplitude modulation.

DETAILED DESCRIPTION

Figure 1A:
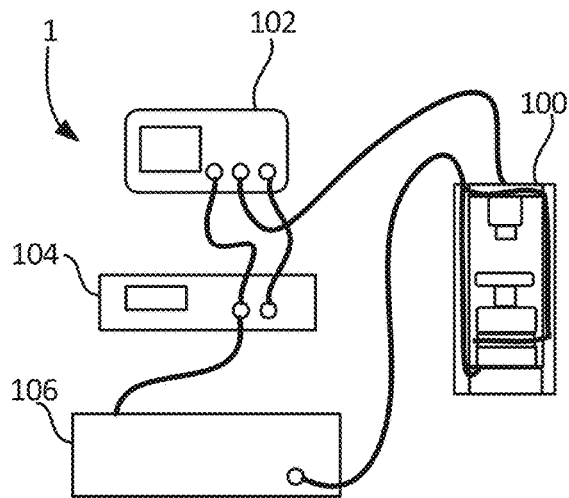
FIG. 1A depicts a schematic of the rheometry system, according to an exemplary embodiment.
Figure 1B:
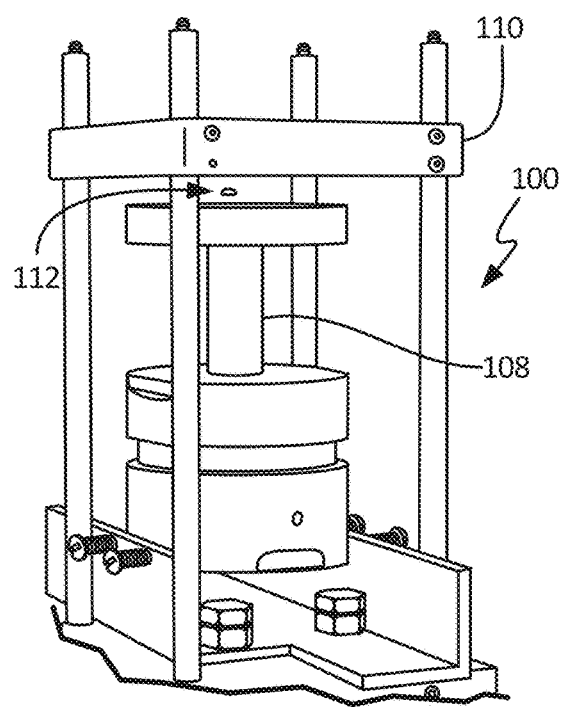
FIG. 1B depicts a perspective view of the an exemplary levitator of the rheometry system, according to one embodiment.

Detailed descriptions of one or more embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The term "biological material" shall mean any biological material, including whole blood, blood clots, soft tissues, and biological and reactive fluids.

The term "optical scattering setup" shall mean any suitable illumination and detection technique in order to capture the frequency, amplitude and phase of the drop oscillation, such as laser scattering or a setup comprising a laser and a photodiode.

All of the known techniques available for the measurement of rheological properties of biological materials (biological fluids, living cells, soft tissues, and bio-engineered materials) described above in the Background section require contact of the sample with the walls of the measuring device. Many biological materials, however, are very sensitive to external environment because they consist of cross-linked networks of reactive proteins or polymers. These networks may reorganize in response to mechanical stimuli induced by the interaction of a biological sample with the rheometer walls, thereby changing the rheological properties of the sample. Tissue samples that regularly come in contact with the walls of a rheological device are at high risk for bacterial contamination. Perhaps most importantly, the accuracy of rheological measurements is reduced because of the uncertainty of the contact boundary conditions. All these observations indicate that the accurate rheological characterization of biological materials can be achieved only by noncontact means.

Liquid drops, gas bubbles, solid particles, and other objects exposed to an acoustic wave field experience acoustic radiation pressure. In the case of intense standing waves, the radiation pressure is significant and can balance the gravitational force, levitating the object at a certain spatial position. Drops in an air or more compressible aqueous host fluid are positioned at the pressure node of the standing wave. The wave amplitude can be modulated to induce static or oscillatory shape deformations of the sample, which may be recorded by a high-resolution digital camera or laser scattering. By careful comparison with theoretical descriptions of deformations and oscillations of drops, the material parameters of the levitated sample can be determined.

To date, no one has combined acoustic levitation with the relationship between bulk viscoelasticity and drop shape oscillation to make bulk rheological measurements of biological or reactive fluids. No non-contact method currently exists for the assessment of the coagulation status of native, stored, or reconstituted whole blood and transfusion therapy guidance. The various embodiments disclosed and contemplated herein relate to methods, devices and systems to achieve noncontact rheometry data on biological materials.

The rheometry system and method embodiments disclosed and contemplated herein relate to the characterization of fluids by way of non-contact means, such as levitation using suitable mathematical descriptions for the inference of the material parameters. As is discussed herein, it is currently believed that accurate rheological characterization of blood clots/thrombi and other biological materials can be achieved only by such means. The various implementations herein relate to devices, systems and methods for assessing the properties of the subject fluids by way of acoustic levitation and the assessment of the viscoelastic properties of the fluids. Such embodiments include systems comprising a novel rheometer. For brevity, each of these implementations will be described herein as a "rheometry system," or "acoustic tweezing rheometer." However, the use of these terms is in no way intended to limit the scope of the described embodiments to a specific modality.

The following extended examples serve to illustrate several aspects of the rheometry system embodiments, including the associated apparatuses and methods. Accordingly, Example 1 illustrates an experimental apparatus and setup used to generate sample data for the rheometry system. Examples 2-4 illustrate the applied theoretical and computational modeling used to extract material properties from measured data. Example 5 illustrates quasistatic deformation and location of bovine blood and gel samples. Examples 6-8 describe in detail the separate types of forcing and the experimental results to be expected from such forcing in the rheometry system. Example 9 describes the calibration for such a rheometry system, using standardized nonbiological samples and comparison with accepted laboratory and commercial rheometers. Example 10 describes the technique by which analytical and computational models will be applied to the determination of viscoelastic drop dynamics. Example 11 illustrates an alternative blood sample formation method to gelling or clotting while levitated, that of preformed samples. Finally, Example 12 describes briefly an expected method for the testing protocol for whole patient blood samples.

Example 1

Acoustic Levitation

Figure 1C:
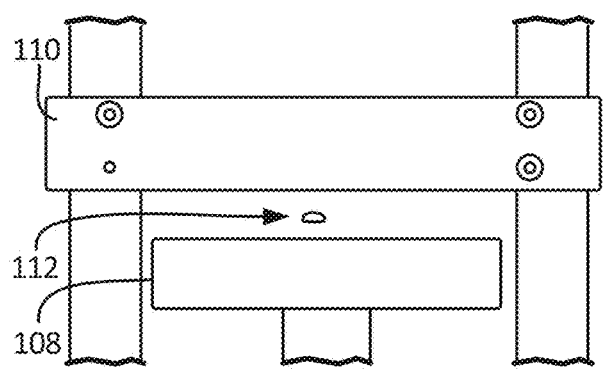
FIG. 1C depicts a close-up side view of a levitating sample, according to the embodiment of FIG. 1B.
Figure 1D:
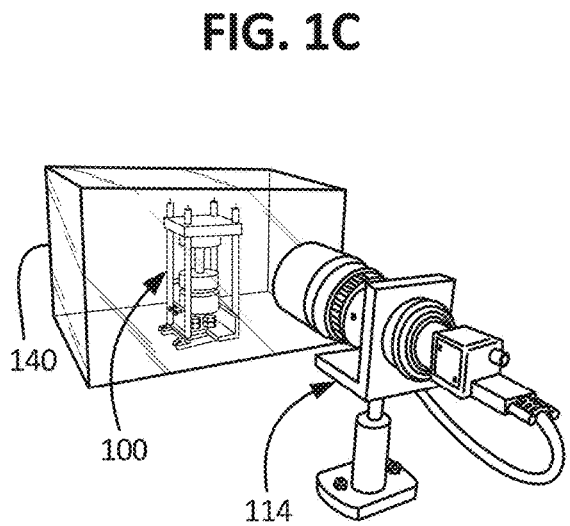
FIG. 1D depicts a perspective view of a camera, according to an exemplary embodiment.
Figure 1E:
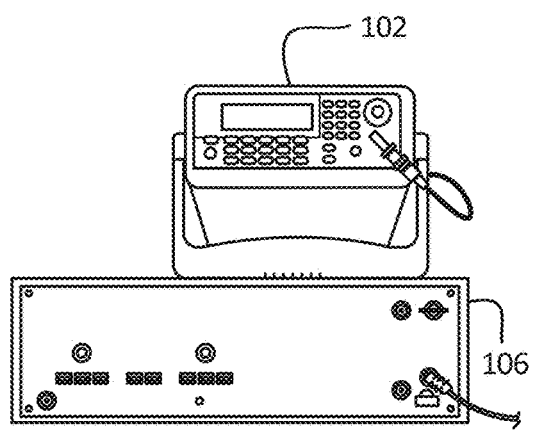
FIG. 1E depicts front view of the function generator and oscilloscope, according to an exemplary embodiment.
Figure 2:
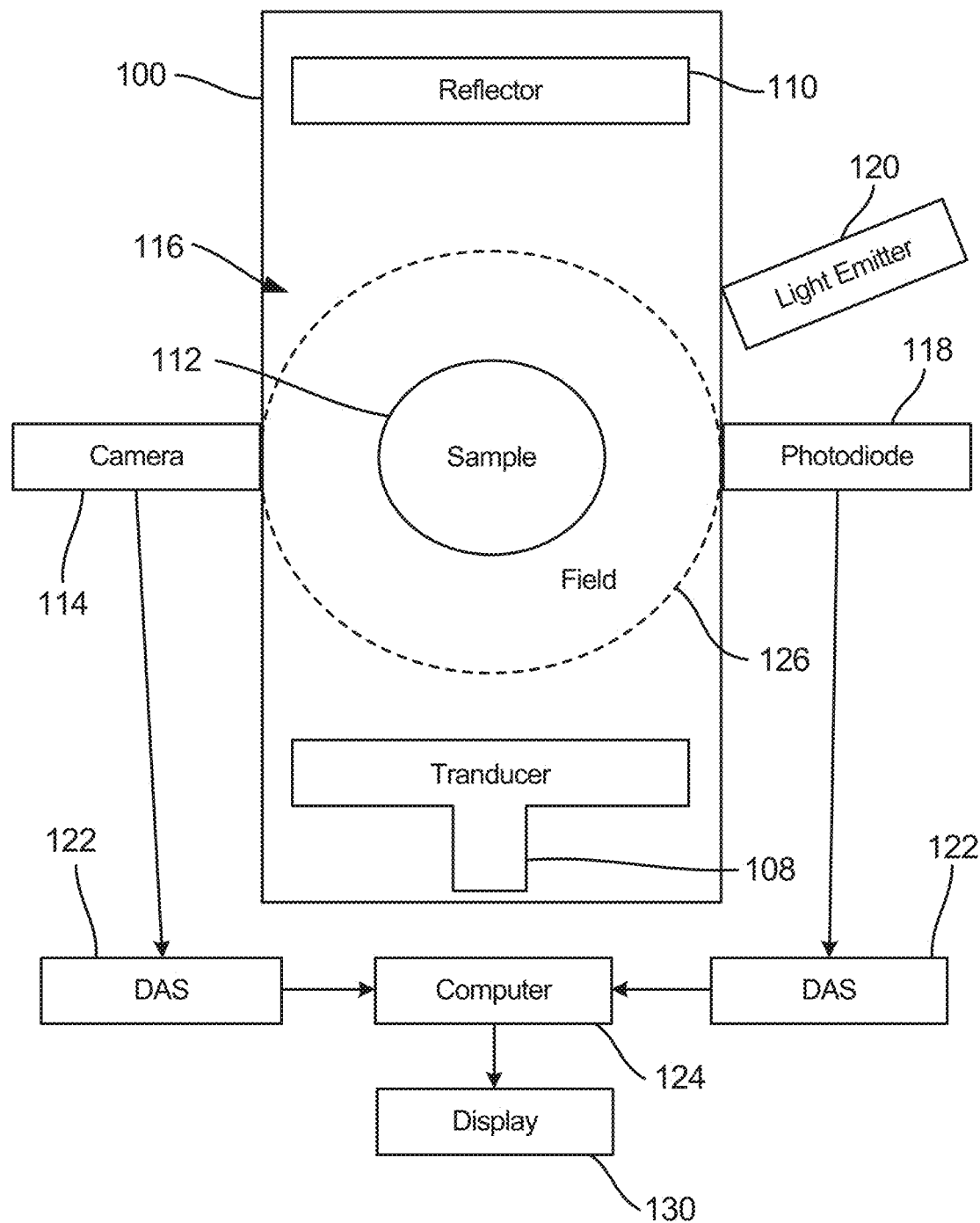
FIG. 2 depicts a block schematic of the rheometry system, according to an exemplary embodiment.

Several exemplary embodiments of the rheometry system 1 and associated components are depicted in FIGS. 1A-1E. FIG. 1A depicts a schematic overview of the rheometry system 1, comprising a levitator 100 that is in operational communication with an oscilloscope 102, a function generator 104, and an amplifier 106. As is shown in FIG. 2B, in exemplary embodiments of the rheometry system 1, the levitator comprises a transducer 108 and reflector 110. FIG. 1C shows a detailed depiction of a sample 112 being levitated according to this embodiment. As is shown in FIG. 1D, in exemplary embodiments, the rheometry system 1 further comprises a camera 114. An implementation comprising the oscilloscope 102 and an amplifier 106 is further shown in FIG. 1E. The use of such embodiments is described herein in reference to FIGS. 2-4B.

FIG. 2 depicts a schematic of an exemplary levitator 100 according to one implementation of the rheometry system 1. In these exemplary embodiments, the levitator 100 comprises a space, cavity or opening 116 adapted to receive the sample, an acoustic reflector 110, a transducer 108, at least one camera 114, at least one photodiode 118. Further embodiments may comprise at least one light emitter 120. As depicted in FIG. 2, the at least one data acquisition system 122 may include the oscilloscope and amplifier (depicted in FIG. 1A), and other means of data acquisition and transmission as would be apparent to one of skill in the art. In use, a small drop of blood or other biological fluid 112 will be dripped into the opening 116, where it will be levitated in a standing acoustic wave field 126 and forced into shape oscillation. The shape deformation of the sample will be recorded using an optical camera 114 and analyzed on a computer 124 using theoretical and computational models. The rheological data will be displayed on a monitor 130. Further implementations may comprise a pressure control system, a pressure vessel and/or housing, though these components are not essential.

Figure 3A:
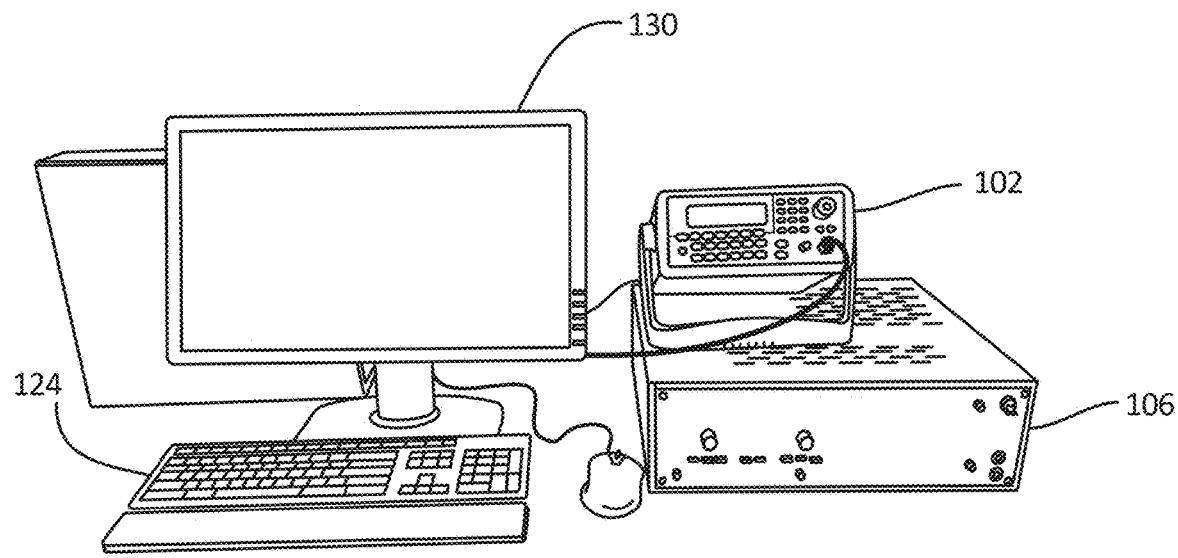
FIG. 3A depicts a front view the rheometry system function generator and oscilloscope connected to a computer and display, according to an exemplary embodiment.
Figure 3B:
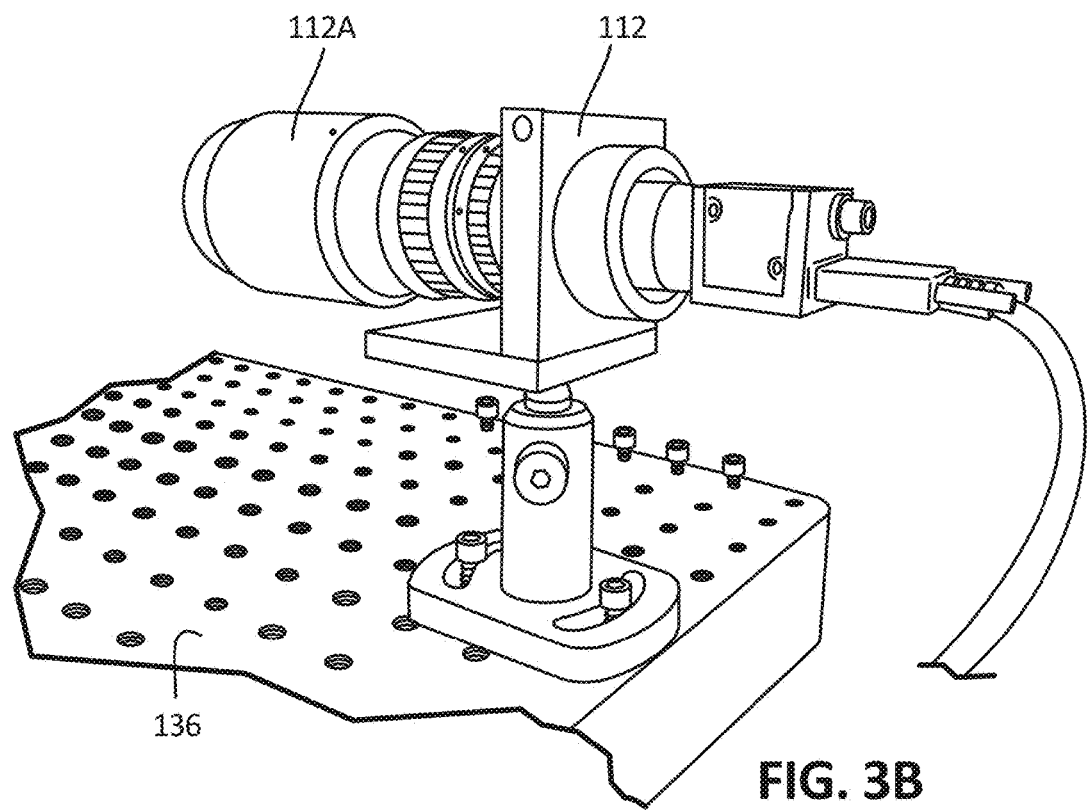
FIG. 3B depicts a rear perspective view of the camera and associated components, according to an exemplary embodiment.

FIGS. 3A-3B depict further aspects of the rheometry system according to certain implementations. In FIG. 3A, and exemplary embodiment of the rheometry system's computer 124, oscilloscope 102 and power amplifier is depicted, while in FIG. 3B, an exemplary digital camera is depicted.

Figure 4A:
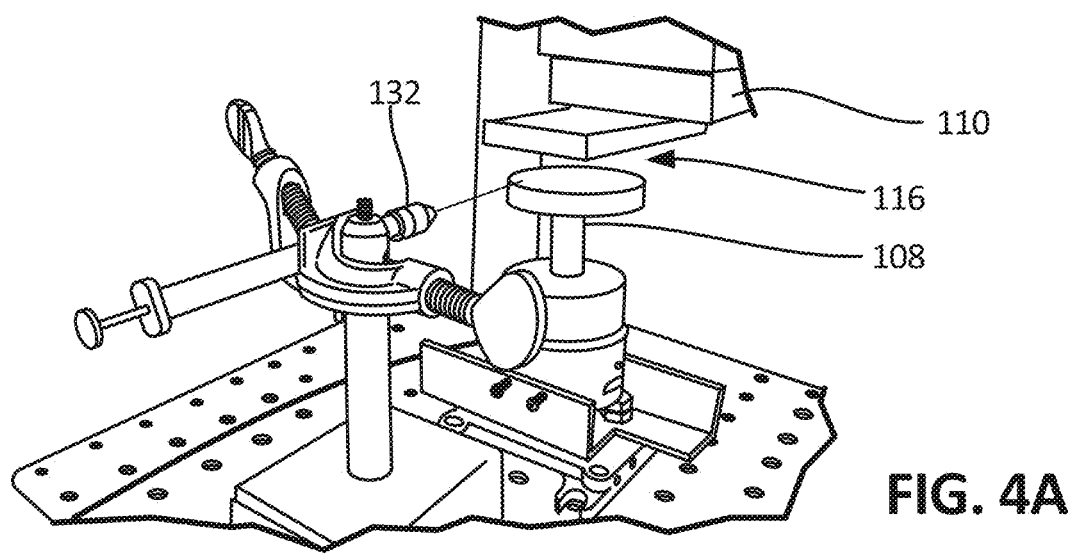
FIG. 4A depicts a perspective view of the input syringe, according to an exemplary embodiment.

FIG. 4A shows an exemplary embodiment of the rheometry system comprising an exemplary sample introduction device 132. In this embodiment, a needle syringe 132 is used to introduce a sample into the opening 116 in a dropwise fashion, such that it is suspended between the reflector 110 and transducer 108. One of skill in the art would understand the various methods that can be used for introducing the sample.

Figure 4B:
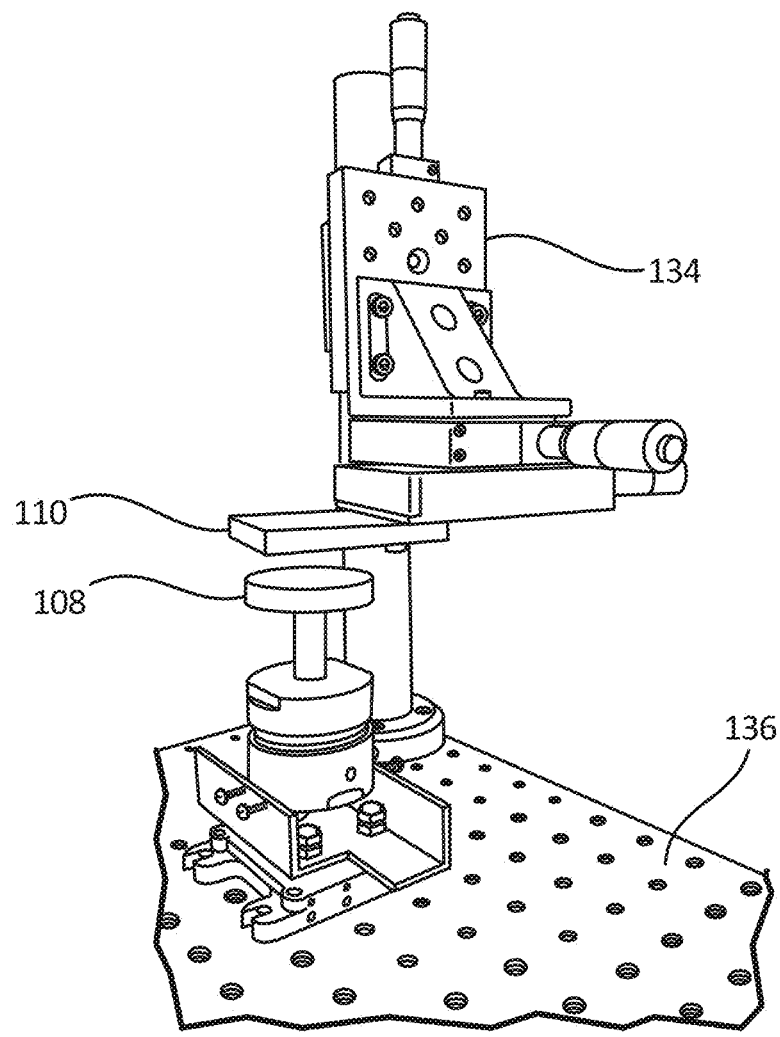
FIG. 4B depicts a perspective view of an embodiment of the rheometry system comprising a three dimensional positioning system.

FIG. 4B depicts an exemplary embodiment of the rheometry system comprising a three dimensional positioning system 134 which is in operational communication with the reflector 110 and otherwise operationally integrated with the system 1.

Thus, in use, a biological fluid sample 112 is inserted dropwise into an opening 116 between the acoustic reflector 110 and transducer 108, where it will be levitated in a standing acoustic wave field and forced into shape oscillation. In these embodiments, a sample is levitated in a host fluid by acoustic radiation forces from a standing acoustic wave field 126. In various applications, the wave field 126 is perturbed by different types of acoustic forcing, leading to static shape deformation (as depicted in FIG. 14) and/or the shape oscillation of the sample (as is shown in relation to FIG. 12).

In certain exemplary implementations, the resulting data can then be passed through analysis software to assess the sample shape oscillation data to extract the values of, and dynamic changes in, the rheological properties of the sample. As described elsewhere herein, this software will implement various mathematical expressions that relate the material constants of a viscoelastic fluid material with the shape oscillation parameters, such as by way of example amplitude and phase, or damping rate and frequency, or location and shape deformation.

As such, and as depicted in FIG. 2, in exemplary embodiments of the system 1, an ultrasonic transducer 108, driven by a function generator and/or amplifier combination, creates an acoustic field 126 around the sample 112. A reflector placed at multiples of $\lambda/2$ results in a standing wave. In some embodiments, a sample may be forced either to a pressure minimum or maximum, in this example, the liquid sample in air host is acoustically levitated at a pressure minimum of the resulting standing wave. For levitating samples on the order of millimeters in diameter, the acoustic pressure is varied sinusoidally at approximately 30 kHz (this is also known as the "carrier" signal). So long as the sample is smaller than the half-wavelength, any levitator can be built to result in any arbitrary frequency standing wave desired by the user to perform the specified rheometry. Generally, at low frequencies the user is limited by the weight of the sample. At high frequencies the sample size tends to become impractically small. Acoustic radiation pressure serves to hold the sample in a fixed position slightly above or below a pressure node, where the gravitational force is balanced.

By way of example, in one exemplary embodiment, two function generators are employed. Other numbers are possible. The first provides the appropriate "carrier" frequency needed to levitate the sample (typically tens of kHz, e.g. 10-100 kHz, however any frequency above 10 kHz may be used), and the second modulates the amplitude of the carrier signal. In certain embodiments, this may be achieved by internal modulation, or external modulation by sources other than function generators. In one embodiment, the amplitude of carrier wave is modulated using step forcing (discussed herein at Example 6). In another embodiment, the amplitude of carrier wave is modulated using a swept-frequency sine (typically 10-1,000 Hz to encompass the resonance frequency of the drop).

To determine the shape, deformation, mode (if any) of oscillation, and vertical location of the sample 112, a camera 114 may be employed. In another embodiment, the camera is cooled CCD digital camera (such as a Retiga 1300, Qimaging) possessing 1300×1024 elements, each capable of yielding 12-bit gray-scale resolution at transfer rates limited only by the IEEE 1394 camera interface. In these embodiments, the frequency and damping of oscillations are obtained by way of an optical scattering setup. In certain exemplary embodiments, a low-power CW He—Ne laser 120 (for example a Melles Griot 05-LP-991) and a large-aperture photodiode 118 (for example an Oriel 8102) with a rise time of 1 μs are employed. In certain other embodiments, other photodiodes are used, such as photodiodes that are not large-aperture. In some embodiments, a user can employ a variety of illumination and detection techniques in order to capture the frequency, amplitude and phase of the drop oscillation with the optical scattering setup. Alternatively, for the oscillatory technique, a single high speed camera could capture all of the above data (shape, deformation, location) instantaneously with sufficient temporal resolution to determine the oscillations, at the expense of large data storage requirements.

As in FIGS. 3A-3B, in one exemplary embodiment of the rheometry system, the levitator 100 is integrated with a high-resolution monochrome digital camera 114 (Basler acA2500) and a Dell computer workstation to record and process the quasistatic deformation and location of levitating samples. By way of example, in certain exemplary implementations, the acoustic levitation system 1 consists of a 70-MHz 4-channel oscilloscope (Agilent DSOX2004A), a 20 MHz function/arbitrary waveform generator (Agilent 33220A), a wideband power amplifier (Krohn-Hite 7500), as well as a transducer and a reflector. In certain embodiments, the transducer is fabricated from piezoelectric elements (Channel Industries) and operates at a frequency of 28 kHz. The reflector is comprised of an aluminum plate as part of the optical cage system (Thorlabs). The output of the amplifier, at a fixed gain of 100, goes to the transducer. The sample 112 is levitated in space between the transducer 108 and reflector 110, and can be enclosed in a transparent environmental control housing (shown as 140 in FIG. 1D) to maintain stable environment during an experiment. Other configurations are of course possible.

In certain embodiments, both the levitator and the digital optical camera are attached to an optical table 136, and the camera 114 is connected directly to the computer 124 via ultra fast USB 3.0. In certain embodiments, the camera can shoot up to 2500×1900 pixel photos at 14 frames per seconds. A zoom macro lens 114A (such as the Navitar Zoom 7000) can be mounted on the camera to provide quality imaging at a working distance of 5 inch. A red light lamp provided backlight behind the levitator. In certain exemplary embodiments, a typical exposure time was between 1 to 3 milliseconds. In certain embodiments, image analysis was performed using the Canny edge detection method in Matlab.

To develop and validate the acoustic levitation technique for the measurement of rheological properties of viscoelastic fluids, levitation experiments with different polymer solutions were utilized to test that the rheological properties of these fluids and their change with time can be captured using acoustic levitation. In exemplary embodiments, the following test fluids were used in these experiments: xanthan gum (0.5% to 2% in water), dextran (1% to 5%), gelatin (2% and 3%), and alginate (3% and 4%). Every experiment began with tuning the transducer to slightly below max output and then injecting a sample into the first node of the standing wave. The typical sample size was about 1 mm in radius. After injection, the sample 112 was lowered until it started to become unstable, moving side-to-side with increasing vigor. This lowering was performed by detuning the transducer on the higher frequency side of its resonance frequency (about 28 kHz). Images are taken by the digital camera approximately every 3 seconds, as the frequency input to the transducer 108 was decreased by steps, moving it closer to the resonance frequency. Induction of deformation continued until the aspect ratio of the sample reached a value between 2 and 3. At this point the frequency was increased again to return the sample to its near-circular, initial shape. Images were taken throughout the increase and decrease in frequency for analysis.

Example 2

Computational Modeling

Drop Deformation in a Viscoelastic Liquid

A numerical algorithm for fully three-dimensional (3-D) transient simulation of incompressible multiphase viscoelastic flows was developed. (Khismatullin D. B., Renardy Y., and Renardy M. *Development and implementation of VOF-PROST for 3D viscoelastic liquid-liquid simulations*. J. Non-Newtonian Fluid Mech. 2006; 140: 120). In this algorithm, the Volume-of-Fluid (VOF) method (Gueyffier D, Li J, Nadim A, Scardovelli R, Zaleski S. *Volume-of-fluid interface tracking with smoothed surface stress methods for three-dimensional flows*. J. Comp. Phys. 1999; 152:423) on a Marker-and-Cell (MAC) grid was used for tracking liquid-liquid interfaces. The Navier-Stokes equations were solved by Chorin's projection method. Viscoelasticity is described by the Giesekus constitutive equation. It was solved by a factorization technique using a semi-implicit scheme. The deformation of a Newtonian drop in a viscoelastic liquid was analyzed under simple shear by the developed method. The algorithm for parabolic reconstruction of the interface was implemented (Renardy Y, Renardy M. *PROST: A parabolic reconstruction of surface tension for the volume-of-fluid method*. Journal of Computational Physics 2002; 183:400) to calculate the surface tension force with high accuracy. Typical shapes of drops at large deformation and during breakup are shown in FIGS. 5A-F.

Leukocyte-Endothelial Adhesion

A 3-D computational model of receptor-mediated leukocyte adhesion to the endothelium or a ligand-coated surface in a parallel plate flow chamber was previously developed. (Khismatullin D, Truskey G. *Three-dimensional numerical simulation of receptor-mediated leukocyte adhesion to surfaces: Effects of cell deformability and viscoelasticity*. Phys Fluids 2005; 17:031505.) In this model, the leukocyte is treated as a compound viscoelastic drop with shell and core phases (cytoplasm and nucleus) of different viscosity and elasticity. A spring-peeling kinetic model was used to describe the receptor-ligand interaction. (Dembo M, Torney D C, Saxman K, Hammer D. *The reaction-limited kinetics of membrane-to-surface adhesion and detachment*. Proc R Soc Lond B Biol Sci 1988; 234:55.) The viscoelasticity of the nucleus and cytoplasm was captured by the Giesekus constitutive equation. This model was applied to study the effect of cell viscoelasticity on shape changes of adherent leukocytes. A monocytic cell line (Mono Mac 6) attached to the lower plate in a parallel plate flow chamber of height 50 μm was considered. (von Andrian U H, Hasslen S R, Nelson R D, Erlandsen S L, Butcher E C. *A central role for microvillous receptor presentation in leukocyte adhesion under flow*. Cell 1995; 82:989.) Two values of the wall shear stress were discussed: 40 dyn/cm2 (high WSS) and 4 dyn/cm2 (low WSS). FIGS. 5A-F depict images of a Newtonian drop in a viscoelastic matrix with We=$\dot{\gamma}\lambda_1$=0.4 and Ca R $\dot{\gamma}\mu_m/\sigma$=0.6 roughly to breakup time. Drop shapes were computed on mesh R/8, domain 32R×8R×8R and time step 0.001 $\dot{\gamma}$. Here $\dot{\gamma}$ is the shear rate, µm the viscosity of the matrix, and σ is surface tension.

FIGS. 5G-L are side view comparisons of computed shapes and in vivo images (FIGS. M-O depict the top view) of the adherent leukocyte. In vivo images show a rolling neutrophil in a postcapillary venule of the rat mesentery (provided by Klaus Ley, Department of Biomedical Engineering, University of Virginia). In this embodiment, the computed shapes correspond to Mono Mac 6 modeled as a compound viscoelastic drop. The cytoplasmic and nuclear viscosities are 35.3 P and 100.0 P, respectively. The cytoplasmic and nuclear relaxation times are 0.176 s and 0.200 s. 252 microvilli of length 0.09 µm are distributed uniformly. The wall shear stress is 40 dyn/cm2.

The simulation showed that if the leukocyte bulk elasticity is negligible, the leukocyte membrane is elongated and disrupted at high WSS. For the viscoelastic case, a transition from a spherical shape to a tear-drop shape typical for rolling leukocytes in vivo was observed (FIG. 5G-Q). The leukocyte was able to roll along the substrate at low WSS. The rolling velocity of the viscoelastic cell was smaller than that of the Newtonian cell, most likely due to the increased deformability of the viscoelastic cell.

Example 3

Extraction of Storage and Loss Moduli for a Non-Biologic Viscoelastic Material Using Acoustic Levitation Acoustic levitation has been successfully utilized to infer viscoelastic properties of a non-biological material, aqueous foam (consisting of water, water-soluble surfactant, glycerol, and air). (McDaniel, J. G. and R. G. Holt, *Measurement of aqueous foam rheology by acoustic levitation.* Physical Review E, 2000. 61(3): p. R2204-R2207; McDaniel, J. G., I. Akhatov, and R. G. Holt, *Inviscid dynamics of a wet foam drop with monodisperse bubble size distribution.* Physics of Fluids, 2002. 14(6): p. 1886-1894; Liu, L., *Development of an Acoustic Levitation Technique to Obtain Foam Material Properties,* in Department of Aerospace and Mechanical Engineering. 2002, Boston University: Boston; Holt, R. G. *Rheology of Foam Near the Order-Disorder Phase Transition.* Final Report for NASA grant NAG#3-2392. June 2005.) The disclosed embodiments utilize acoustic levitation to establish the viscoelastic properties of biological material.

In the disclosed example, data for frequency and damping for the n=2 (prolate-oblate, or quadrupole) shape oscillation mode of a spheroidal foam sample were obtained for a variety of sample sizes and gas volume concentration (labeled "void fraction" in the plots). The data were obtained using a swept-frequency sinusoidal modulation of the acoustic field amplitude.

Inference of the shear modulus (a measure of the elastic property of a fluid) was obtained from the frequency $\omega_s$ of the sample mode oscillation using the following analytic expression:

$$G = \rho \left(\frac{\omega_s R}{\xi}\right)^2 \frac{1-2v}{2(1-v)} \quad (1)$$

with v the Poisson's ratio, R the radius of the foam sample (assumed spherical), ρ the foam density and ξ the wavenumber. An average value for both the Poisson's ratio (0.35) and normalized wavenumber (1.2) for the shape oscillation model was utilized. Image analysis yielded both the mean bubble size, and the foam sample shape and volume. After a frequency sweep experiment was finished, the foam sample was captured and weighed on a scale with 0.01 mg resolution, which when combined with the image data yields the density for a sample.

Figure 6A:
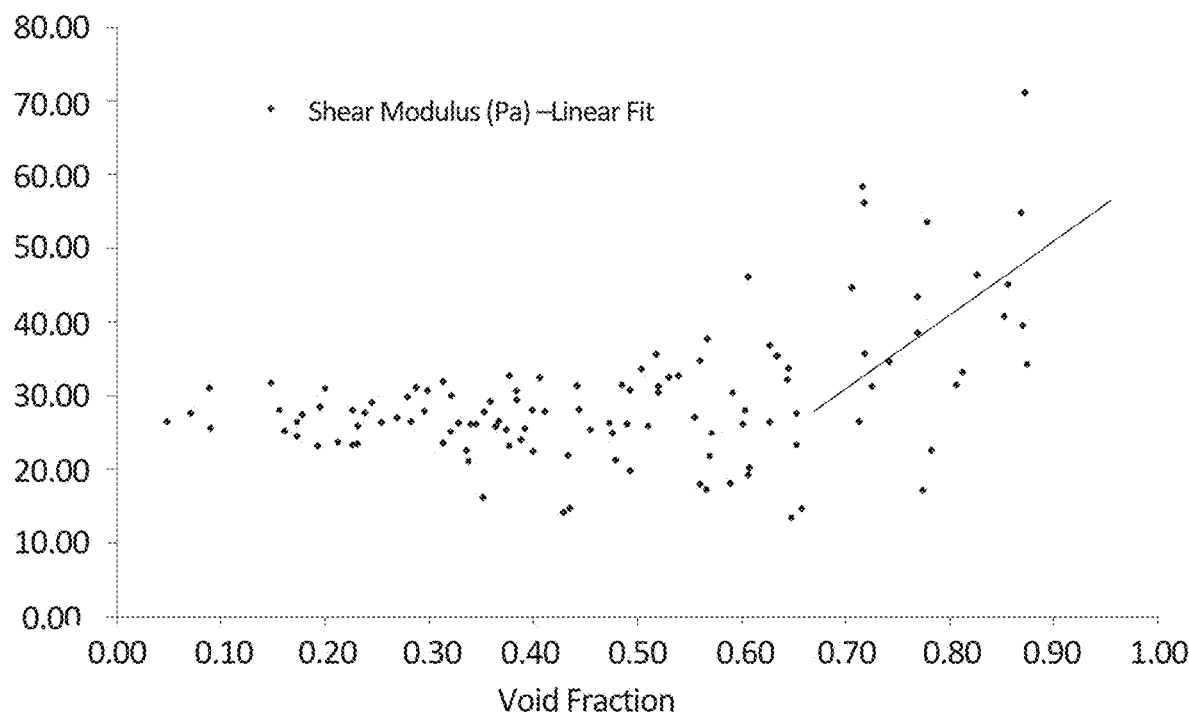
FIG. 6A is a graphical representation of shear elastic (storage) modulus of an aqueous foam drop obtained from an exemplary acoustic levitation method.
Figure 6B:
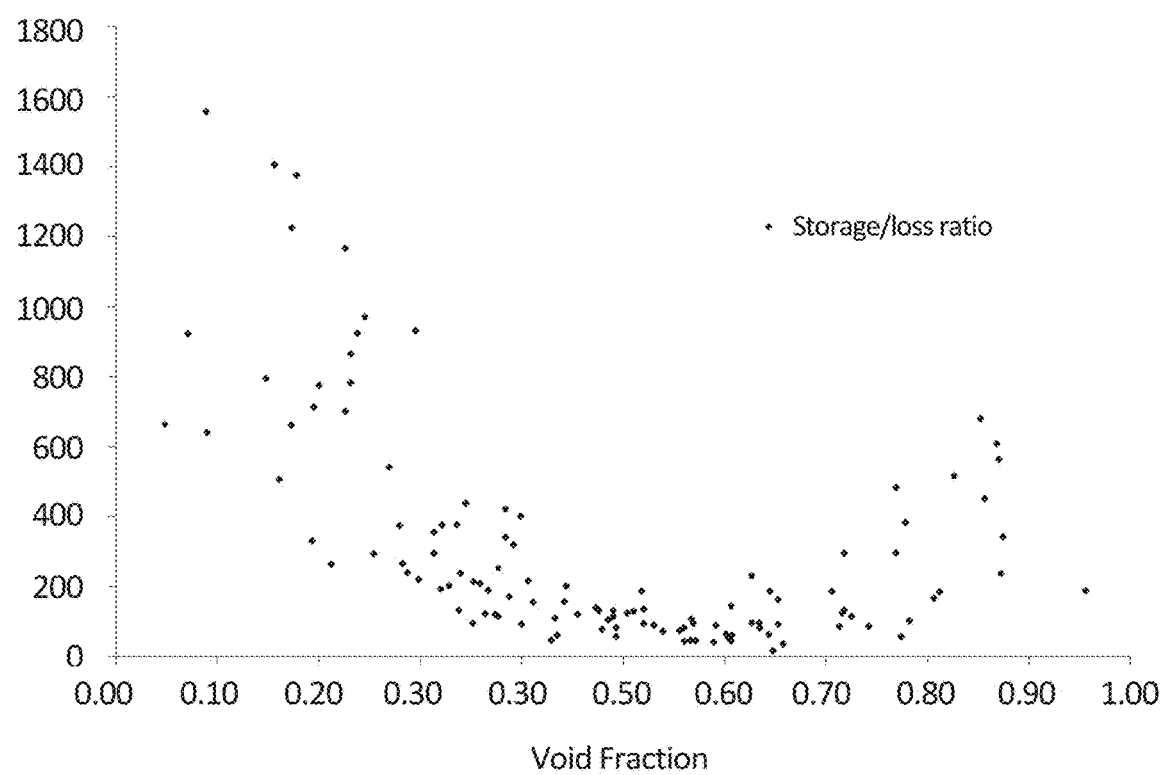
FIG. 6B a graphical representation of ratio of elastic (storage) modulus to loss modulus for aqueous foam data obtained from an exemplary acoustic levitation method.

Data from this example is represented in FIGS. 6A-6B. FIG. 6A is a graphical representation of shear elastic (storage) modulus of an aqueous foam drop obtained from an exemplary acoustic levitation method. FIG. 6B depicts a graphical representation of ratio of elastic (storage) modulus to loss modulus for aqueous foam data obtained from an exemplary acoustic levitation method.

Turning to these figures in greater detail, FIG. 6A depicts an exemplary shear modulus plot. For void fractions below 0.67, the shear modulus represents a measure of the surface tension of the liquid phase of the foam samples, and is therefore a constant within experimental error. While this is unique to foams, it is not necessarily a feature of biological materials, such as blood clots. As the foam becomes an effective solid, the modulus is seen to increase with void fraction. An order of magnitude linear fit to the data in the elastic region above 0.67 yields the following dependence: $G=100(\varphi-0.67)+28$, where G (in Pa) is the shear elastic modulus, and $\varphi$ is the void fraction. This technique is able to resolve shear moduli on the order of 100 Pa, a value which is quite small compared to the estimates of blood clot modulus of roughly 2500 Pa from commercial rheometer tests of a whole blood clot.

Loss modulus is a measure of the viscous property of a fluid. To measure loss modulus as the unitless damping ratio $\zeta$ of the linear drop oscillation, the phase lag of the oscillation relative to the forcing as the frequency sweep progresses in the present system is given by:

$$\phi = \arctan\left(\frac{2\zeta\omega\omega_s}{(\omega_s^2 - \omega^2)}\right) \quad (2)$$

The embodiments of the present system therefore define loss modulus as:

$$\zeta = \frac{1}{\omega_s (d\phi/d\omega)|_{\omega_s}}. \quad (3)$$

such that it is fully determined by the slope of the phase curve evaluated at the sample resonance frequency $\omega_s$. The ratio of the shear or storage modulus and the loss modulus as shown in FIG. 6B. The main feature in this plot is the appearance of a minimum in the ratio at or near 0.67 in the void fraction, corresponding to a maximum in the damping at the critical void fraction. This data demonstrates that the presently disclosed levitation system is capable of sensitive determinations of drop behavior.

Example 4

Small-Amplitude Theory for Shape Oscillation of a Viscoelastic Drop and its Use to Measure the Mechanical Properties of Individual Living Cells The presently disclosed levitation system comprises a novel approach to assessing the mechanical properties of biological samples by way of small-amplitude theory. In microgravity, an incompressible liquid drop assumes a spherical shape at equilibrium, which can be perturbed by external means. When the external perturbation is removed, the drop eventually returns to its original spherical form. Depending upon the bulk properties of the liquid and the surface parameters this process may take the form of underdamped oscillations about or overdamped aperiodic decay toward the spherical shape. For example, using the linear Jeffreys constitutive equation:

$$\tau + \lambda_1 \frac{\partial \tau}{\partial t} = 2\mu \left( \dot{\gamma} + \lambda_2 \frac{\partial \dot{\gamma}}{\partial t} \right), \dot{\gamma} = \frac{1}{2} (\nabla v + \nabla v^T), \quad (4)$$

The effects of bulk viscoelasticity on normal mode oscillations of non-biological liquid drops under zero gravity was established. (Khismatullin D B, Nadim A. Shape oscillations of a viscoelastic drop. Phys Rev E Stat Nonlin Soft Matter Phys 2001; 63:061508.). Here $\tau$ and $\dot{\gamma}$ define the shear stress and rate-of-strain tensors, v the velocity vector, $\mu$ the shear viscosity, and $\lambda_1$ and $\lambda_2$ are the relaxation and retardation times of the viscoelastic material.

In this example, the present system performs this analysis for biological samples by expressing the surface profile of the drop in terms of the Legendre polynomials and using perturbation analysis. The characteristic equation for the frequency and damping rate of shape oscillations was derived. The use of this equation was subsequently analyzed in the high- and low-viscosity regimes and solved numerically at intermediate values of viscosity in the case of quadrupole oscillations to establish the efficacy of the system. Under these conditions, the elasticity of the material gave rise to a novel shape oscillation present even if the material viscosity is greater than a critical value, as Newtonian drops cease to oscillate in air at a viscosity greater than 0.65 poise. In the high-viscosity limit, this elastic oscillation was independent of surface tension. Its angular frequency $\omega_s$ and damping rate $\delta_s$ were functions of viscoelastic parameters, density of the material $\rho$, its equilibrium radius R, and the mode of the oscillation n:

$$\omega_s \approx \sqrt{\frac{2(n-1)(2n^2+4n+3)\mu}{(2n+1)(1+E_n)\rho R^2 \lambda_1}}, \quad (5)$$

$$\delta_s \approx \frac{1}{2\lambda_1} + \frac{(n-1)(2n^2+4n+3)\mu\lambda_2}{(2n+1)(1+E_n)\rho R^2 \lambda_1},$$

$$E_n = \frac{4n(n-1)(n+2)}{(2n+1)(2n+3)(2n+5)}.$$

Correspondingly, in the low-viscosity limit, the expressions for the frequency and damping rate of surface-tension-driven oscillations were derived, containing corrections due to material elasticity. It was demonstrated through numerical analysis that equations (5) realistically described shape oscillations of the material in the case when both viscosity and elasticity are significant. Thus, in the present system equations (5) can be used to determine viscoelasticity of the material from drop oscillation experiments. According to these equations, in a particular case of quadrupole oscillations (n=2) and at $\lambda_2$=0 (the ratio of the retardation time to the relaxation time is small for most biological and polymeric fluids), the viscosity and relaxation time depend on the oscillation frequency and damping rate as:

$$\mu = \frac{347}{4788} \frac{\rho R^2 \omega_s^2}{\delta_s}, \lambda_1 = \frac{1}{2\delta_s}. \quad (6)$$

By measuring the light scattering from living cells, it has been demonstrated that Jurkat cells excited by an acoustic wave undergo elasticity-driven free oscillation. (Georgescu R, Khismatullin D, Holt R G, Castagner J L, A'amar O, Bigio I J. Design of a system to measure light scattering from individual cells excited by an acoustic wave. Optics Express 2008; 16:3496.) Ultrasound excitation of Jurkat cells resulted in a resonant peak in the spectrum of the scattered signal centered at the frequency of around 20 kHz. This peak was not observed when the ultrasound transducer was off and was a result of shape oscillation of Jurkat cell's nucleus (the cell nucleus provides the strongest optical scattering).

The disclosed system (Eq. (5)) predicts that the natural frequency of the Jurkat cell's nucleus shape oscillation is 17.3 kHz provided the nucleus radius and density are 4 μm and 1040 kg/m$^3$ and the nucleus viscosity and relaxation time are in range of experimental values (5 Pa·s and 0.176 s). Exemplary embodiments of the system can be used to determine the mechanical properties of individual living cells from light scattering data by using the theory of viscoelastic drop oscillation.

Example 5

Quasistatic Deformation and Location of Bovine Blood, and Gel Samples

Figure 7A:
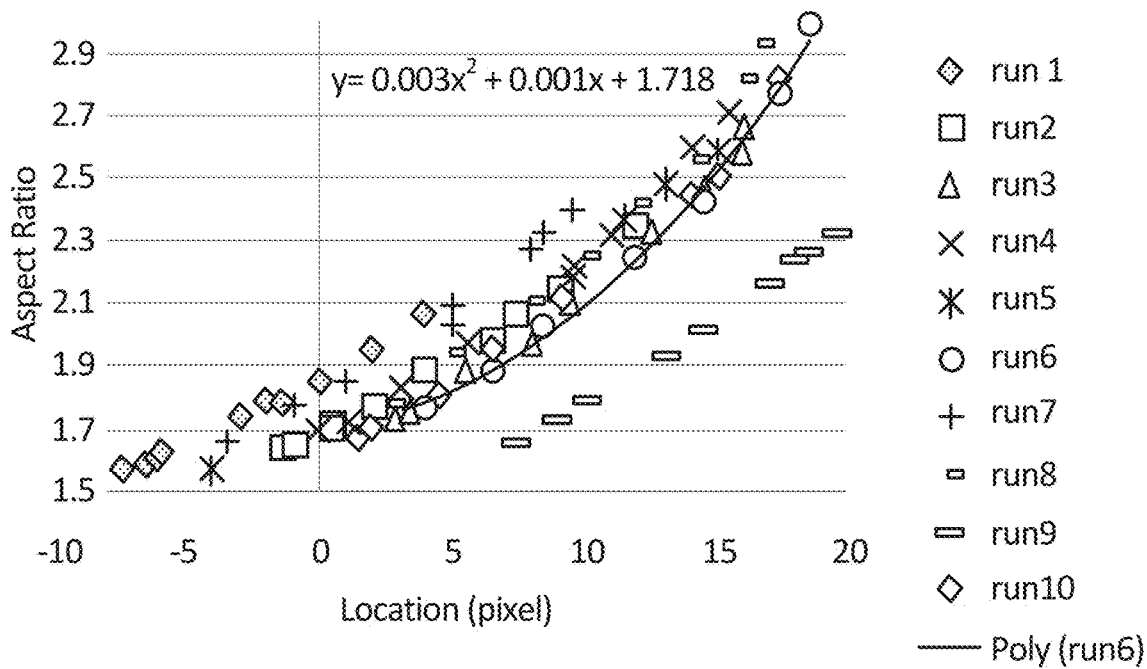
FIG. 7A is a graphical representation of deformation (ratio of long axis to short axis of elipsoid) vs. location along the vertical axis in the levitator of a bovine blood drop coated with a thin layer of silicone oil to retard evaporation.
Figure 7B:
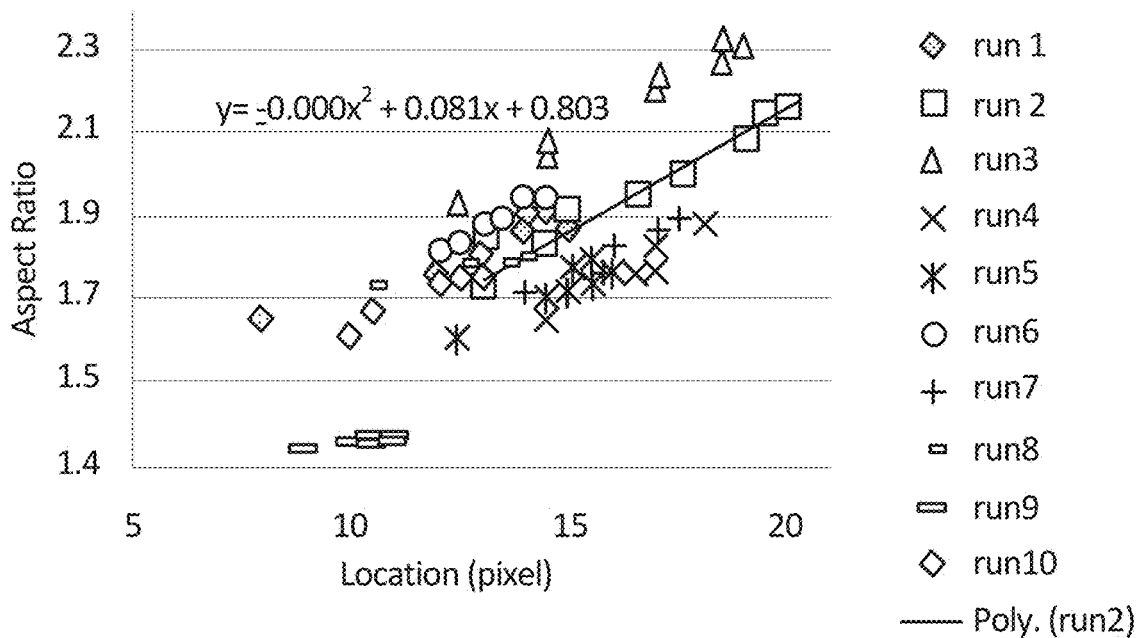
FIG. 7B is a graphical representation of deformation vs. location of a bovine blood clot sample coated with a thin layer of baby oil to retard evaporation.
Figure 8A:
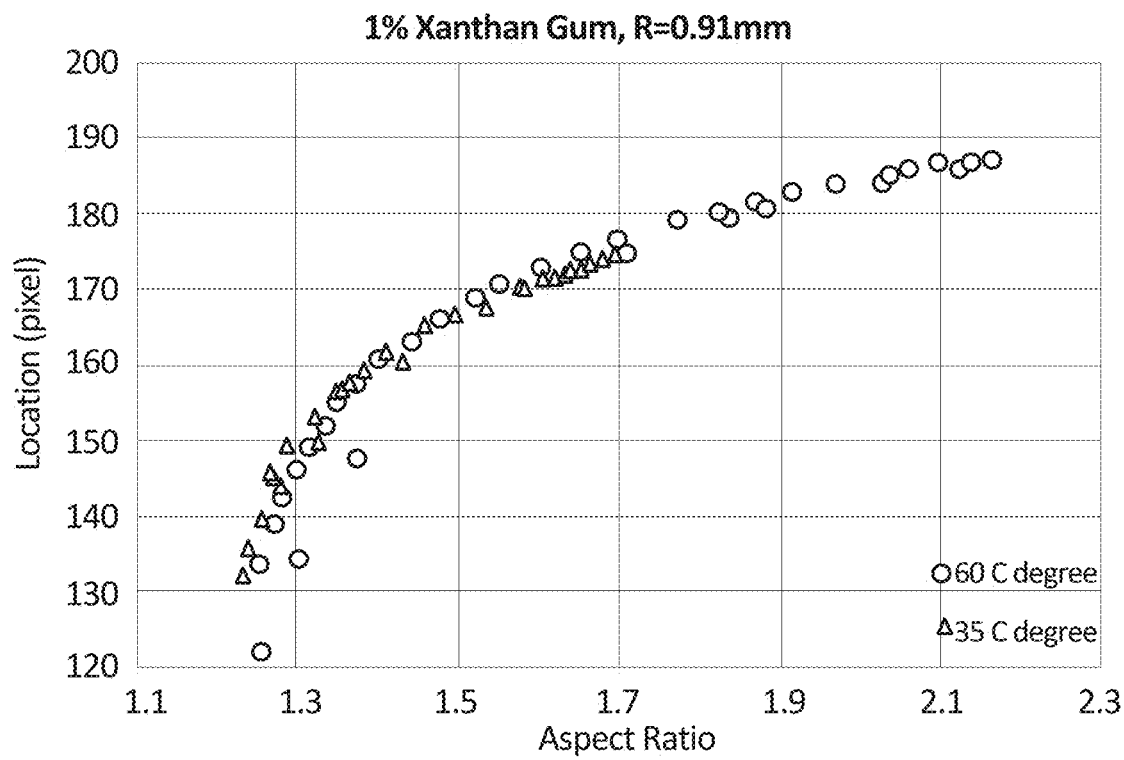
FIG. 8A is a graphical representation of the effect of temperature and polymer concentration on the deformation of levitating 1% xanthan gum.
Figure 8B:
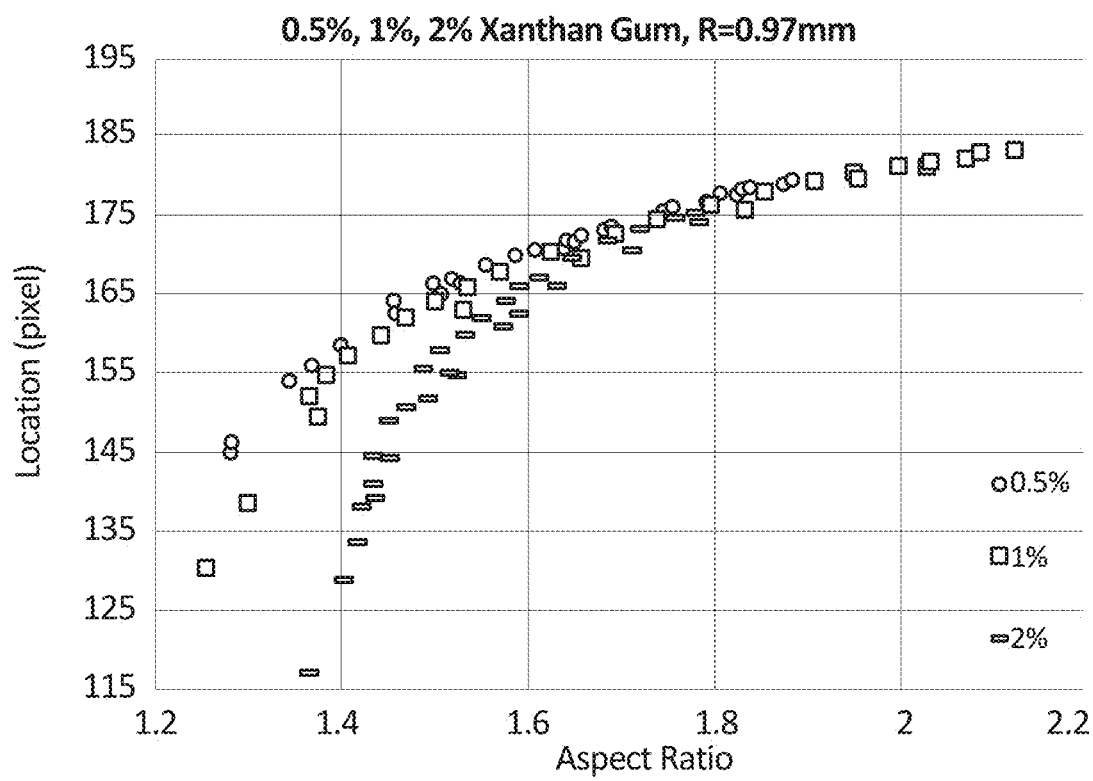
FIG. 8B is a graphical representation of the effect of temperature and polymer concentration on the deformation of levitating 0.5% xanthan gum.

In a further example, data on quasistatic deformation and location of bovine blood and bovine blood clots was assessed to demonstrate the efficacy of the present system as applied to these biological samples. The combination of deformation and location in an acoustic field is a unique signature of the material properties. FIG. 7A shows the deformation (plotted as aspect ratio) vs. height of a drop of blood, for a variety of drop sizes. In this example, the characteristic curve shape is common to all drops regardless of size. FIG. 7B depicts the same plot for a bovine blood clot coated with oil to suppress evaporation). In this example, the characteristic curve is nearly linear (as opposed to the power-law shape of blood) and the achievable range of aspect ratio is much smaller owing to the stiffness of the clot. These quasistatic examples have been plotted as aspect ratio vs. location curves in FIGS. 8A-11B. In these examples, the aspect ratio (defined here as the ratio of sample width to sample height) is a measure of sample deformation, while the sample location (defined here as height of the sample centroid above the transducer surface) is directly related to the input conditions (e.g., the driving frequency). At low aspect ratios, a levitating sample is below the node, however as it becomes increasingly deformed, the sample approaches the node. This finding explains the saturation-like curves of the aspect ratio vs. location we got. Using xanthan gum, we showed that temperature has an insignificant effect on sample deformation (FIG. 8A), therefore the system is not sensitive to temperature changes, which is important for its use for whole blood coagulation monitoring. FIG. 8B demonstrates that there is a substantial change in the lower portion of the aspect ratio vs. location curve when the xanthan gum concentration (and thus the sample elasticity) increases. This indicates that the system is sensitive to the elastic properties of the sample, and thus it can be used to measure the sample elasticity.

Figure 9A:
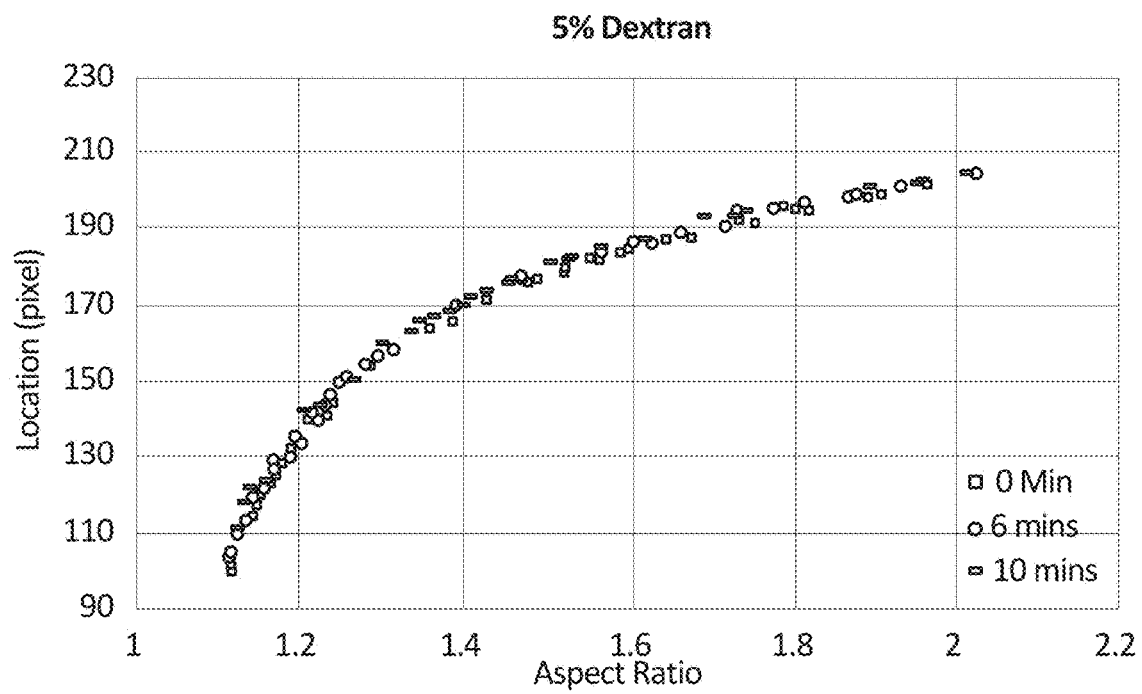
FIG. 9A is a graphical representation of the deformation of levitating dextran droplets over time.
Figure 9B:
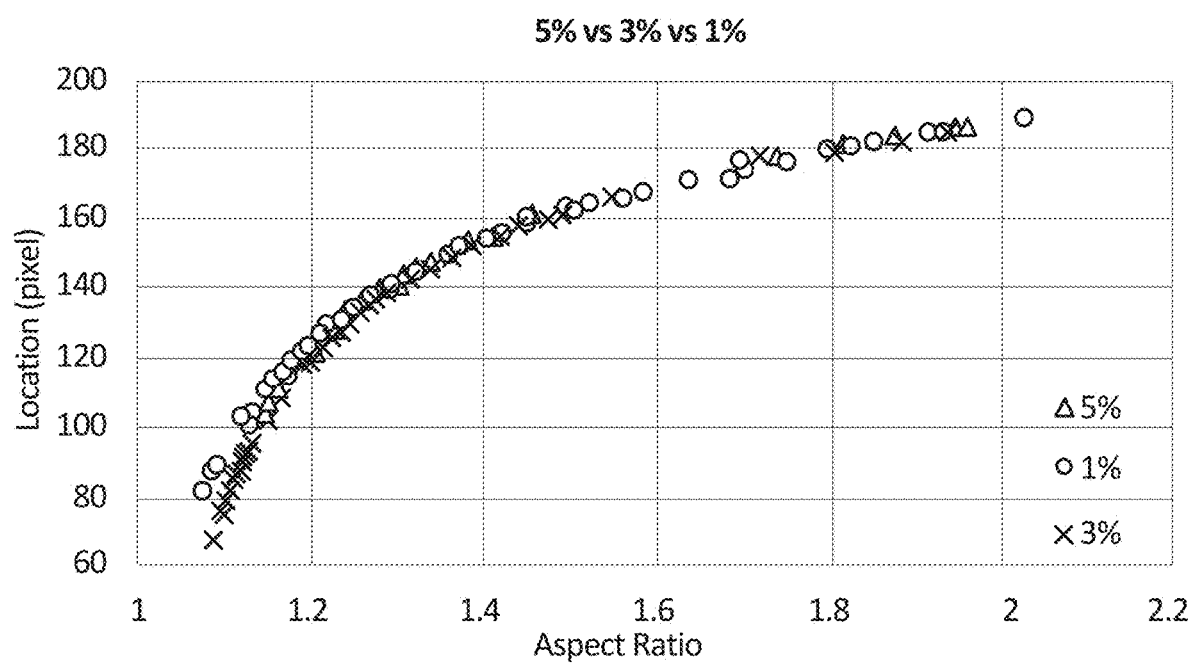
FIG. 9B is a graphical representation of the deformation of levitating dextran droplets at varying concentrations.

FIG. 9A-B show the levitation data for dextran droplets. Dextran in water behaves as a Newtonian fluid (i.e., it has no elastic properties) even at high polymer concentration. Indeed, we see no change in the aspect ratio vs. location curves for this material with time (FIG. 9A) or polymer concentration increase (FIG. 9B). Thus, using the aspect ratio vs. location data we can detect whether a specific material shows viscoelastic properties (as in the case of xanthan gum, FIG. 8) or it behaves as a simple Newtonian fluid (as in the case of xanthan gum, FIGS. 9A-B). The data in FIG. 9A-9B also indicate that the quasistatic deformation tests can measure the sample elasticity (which is a key feature in whole blood coagulation monitoring) but not the sample viscosity.

Figure 10:
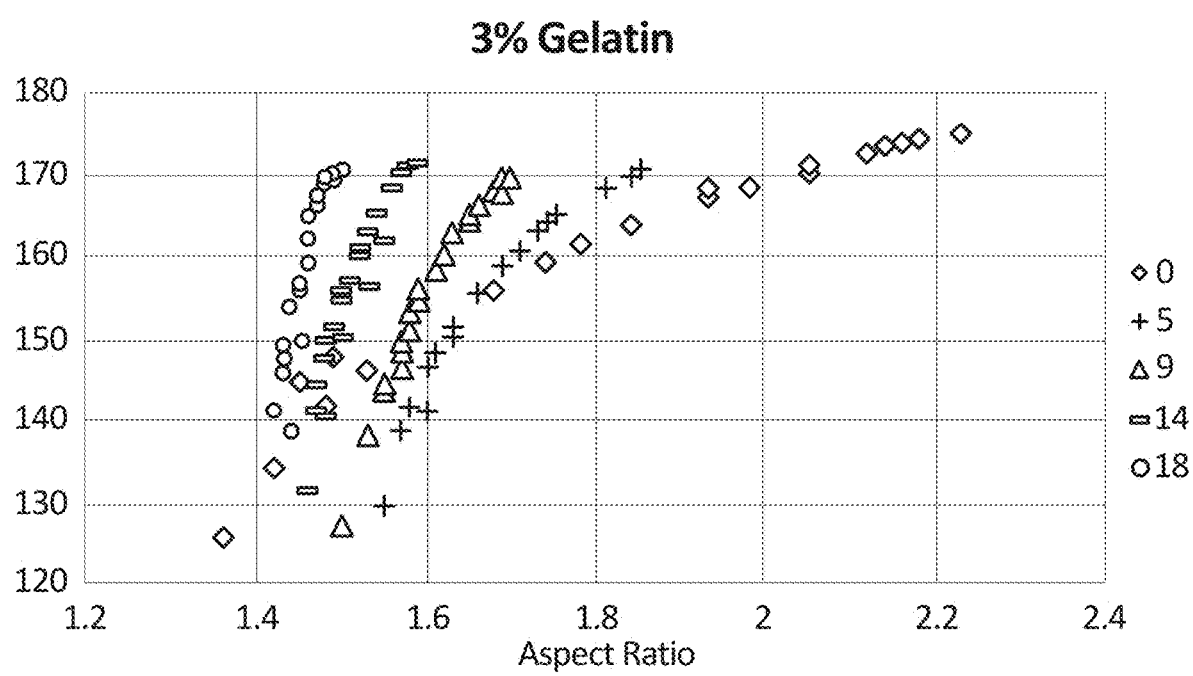
FIG. 10 depicts the deformation of levitating gelatin droplets over time.

When gelatin or alginate are dilated in water, they form hydrogels characterized by much higher stiffness that the initial solutions of these polymers. In many mechanical aspects, blood coagulation is similar to gelation. Thus, as the examples shown in FIGS. 10 and 11A-B demonstrate, the quasistatic deformation assessments of certain embodiments are able to capture changes in the sample elasticity during gelation. Specifically, the aspect ratio vs. location curve becomes steeper for 3% gelatin droplets over the course of 18 minutes from the injection of the sample into the levitator, during which time the sample typically becomes completely gelled (FIG. 10).

Alginate is also a very common used biological hydrogel. Alginate in water is a highly viscous liquid that does not start gelling without exposure to calcium ions. In a further example, a glucono-delta-lactone (GDL) solution was used to initiate alginate gelation.

Figure 11A:
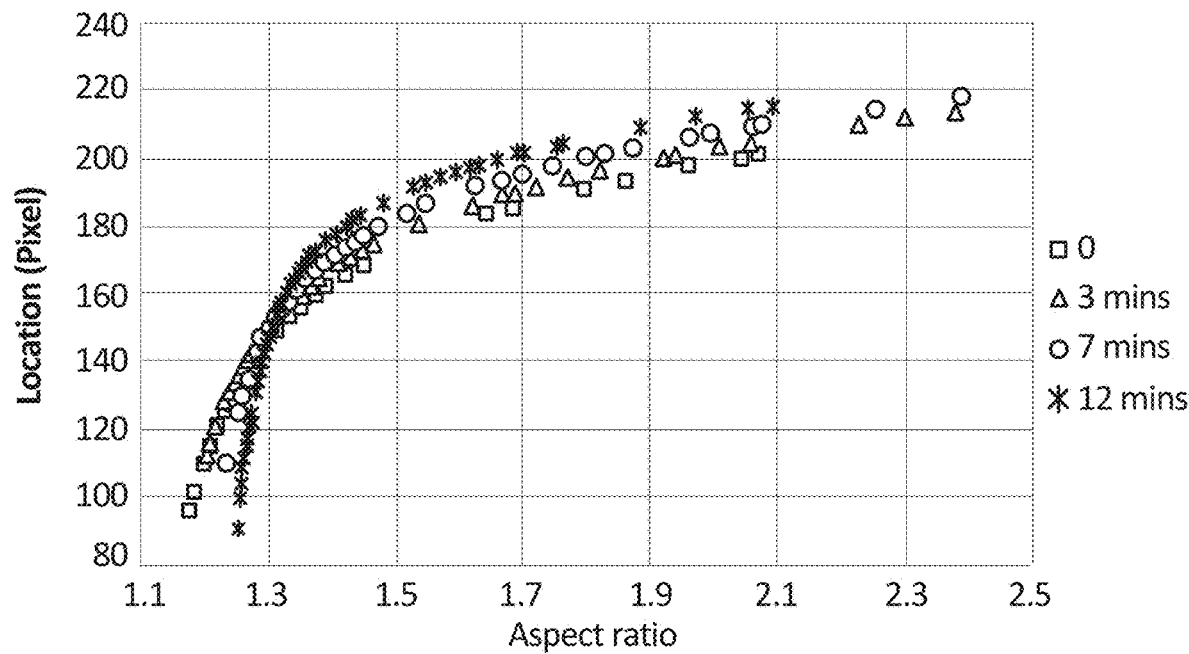
FIG. 11A depicts the deformation of levitating 3% alginate droplets exposed to 6% over time.

The example of FIG. 11A shows that the slope of the lower portion of the aspect ratio vs. location curve for 3% alginate dramatically increases with time (in this example over 12 minutes) when alginate is exposed to 6% GDL.

Figure 11B:
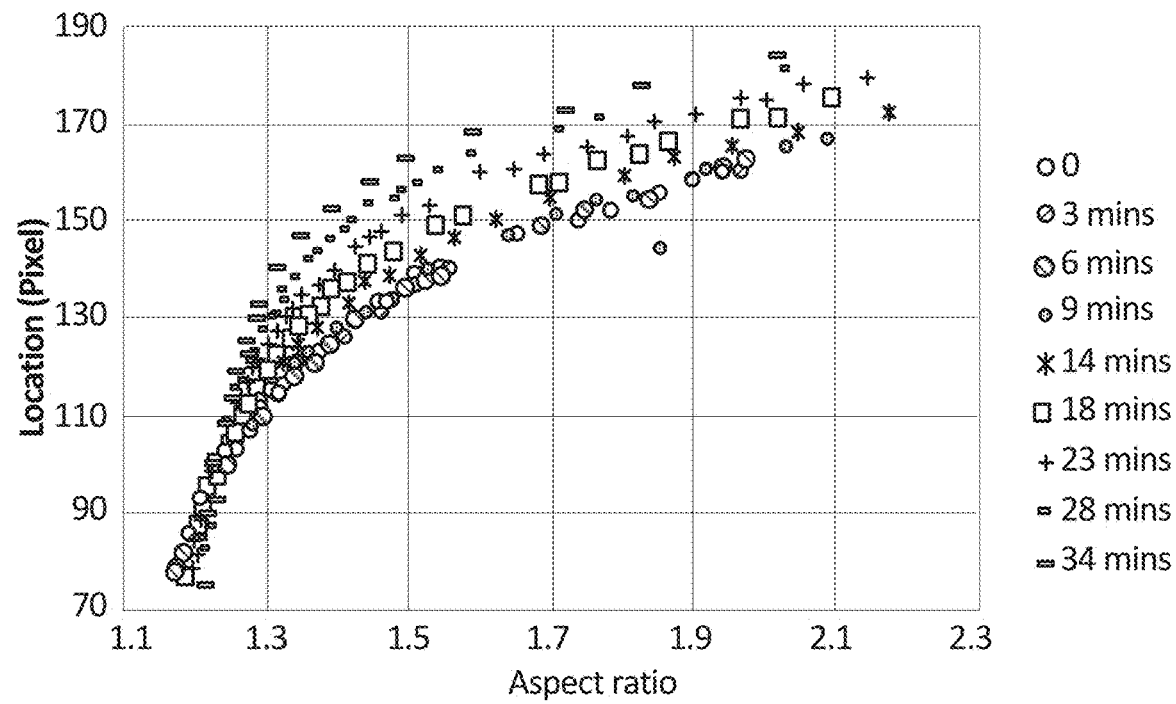
FIG. 11B depicts the deformation of levitating 4% alginate droplets exposed to 6% over time.

FIG. 11B depicts an example in which the gelation of alginate starts approximately 9 minutes after the alginate droplet injection into the rheometry system. Thus, in certain embodiments of the rheometry system, the time needed for gelation can be calculated, which is functionally equivalent to the prothrombin time (PT) or partial thromboplastin time (PTT) in colagualtion tests with blood plasma or whole blood. As such, the rheometry system can be used to calculate the rheological properties of a biological material.

Example 6

Step Forcing

In a further application of an embodiment of the rheometry system in no-gravity conditions, acoustic pressure amplitude may be either increased or decreased in a sudden (as defined by rise time less than the relaxation time of the drop sample) manner by way of a step change in the modulation voltage during levitation. In certain embodiments, the acoustic pressure amplitude can be increased or decreased by a rise time of approximately 1ms. Other times are possible. When this change in pressure is induced, the levitated sample relaxes to the equilibrium shape dictated by the balance of mechanical stress. By way of example, when the sample material is underdamped, such relaxation occurs by way of freely decaying shape oscillations, as is shown in FIGS. 12A-H for water drops. These depict a sequence of four video frames (X-view at A, C, E and G; corresponding Z-view at B, D, F, and H) depicting a cycle of the normal mode oscillation (n=2, or quadrupole mode) of a spheroidal sample in an acoustic levitator. The frequency and damping may then be related to the model-dependent viscoelastic parameters identified in the analysis above, described below.

Example 7

Swept-Frequency Sine Forcing

Figure 13A:
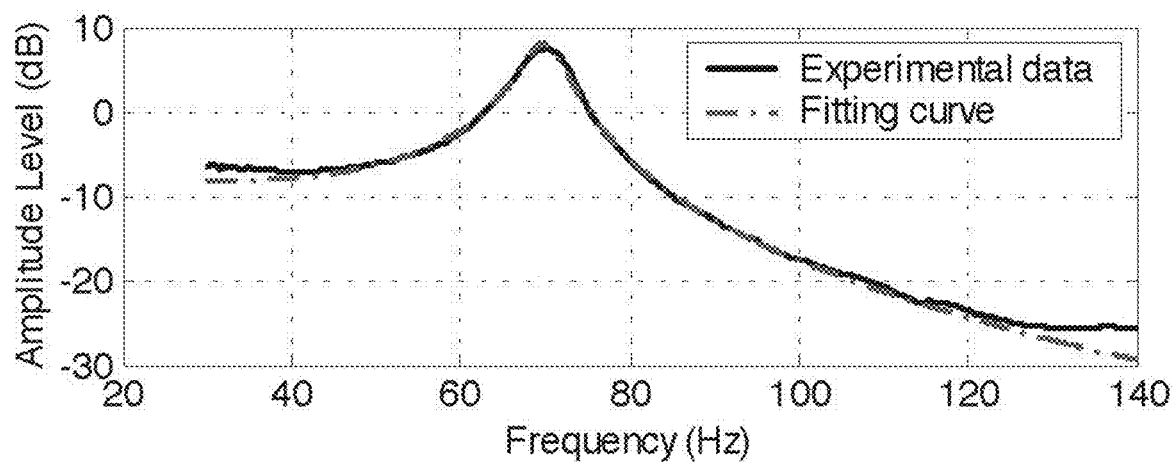
FIG. 13A depicts the amplitude vs. frequency of detected scattered laser light from an acoustically levitated sample subjected to swept-frequency sine forcing from 30 to 130 Hz modulation frequency and a linear viscous model, according to one embodiment.

In one embodiment, the amplitude modulation is sinusoidal. The modulation frequency is then swept to include at least one normal mode of oscillation. In a preferred embodiment, resonant samples are used. In other embodiments, samples not underdamped may be used. The amplitude and phase of the sample oscillation is then obtained from the scattered laser light incident on the photodiode. FIG. 13A depicts the amplitude vs. frequency of detected scattered laser light from an acoustically levitated sample subjected to swept-frequency sine forcing from 30 to 130 Hz modulation frequency. A fit to a linear viscous model is also shown.

Figure 13B:
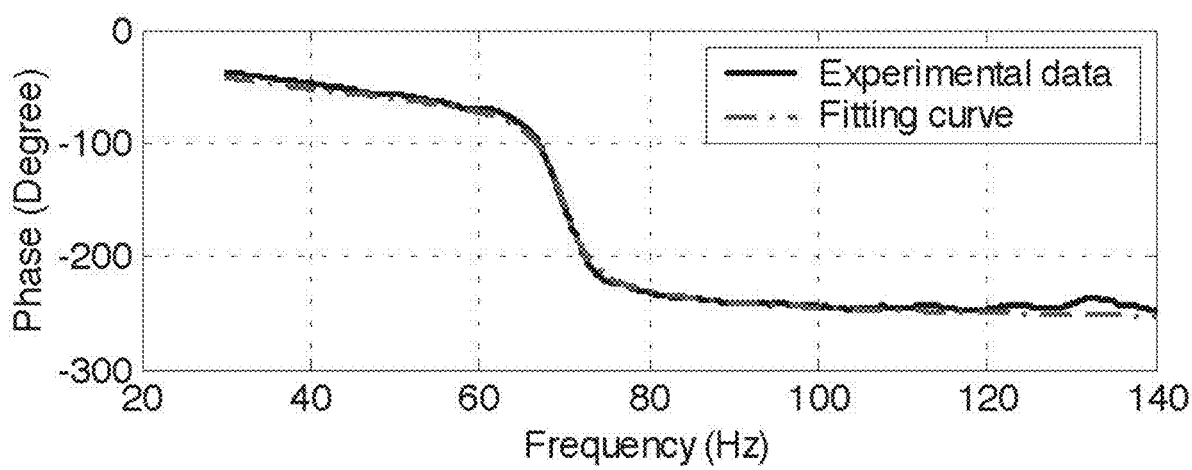
FIG. 13B depicts the phase vs. frequency of detected scattered laser light from an acoustically levitated sample subjected to swept-frequency sine forcing from 30 to 130 Hz modulation frequency and a linear viscous model, according to one embodiment.

FIG. 13B depicts the phase vs. frequency of detected scattered laser light from an acoustically levitated sample subjected to swept-frequency sine forcing from 30 to 130 Hz modulation frequency. A fit to a linear viscous model is also shown. These results were obtained using an aqueous foam sample, using methods from McDaniel, J. G. and R. G. Holt, *Measurement of aqueous foam rheology by acoustic levitation*. Physical Review E, 2000. 61(3): p. R2204-R2207; McDaniel, J. G., I. Akhatov, and R. G. Holt, *Inviscid dynamics of a wet foam drop with monodisperse bubble size distribution*. Physics of Fluids, 2002. 14(6): p. 1886-1894; Liu, L., *Development of an Acoustic Levitation Technique to Obtain Foam Material Properties*, in *Department of Aerospace and Mechanical Engineering*. 2002, Boston University: Boston).

By performing such experiments for a variety of material parameters and sample sizes in embodiments of the rheometry system, the relevant material properties may be extracted by applying the modeling disclosed below, which is a departure from the modeling above under no-gravity conditions.

Example 8

Ramp Forcing

The acoustic pressure amplitude may also be increased in a linear fashion over time (ramp), slowly so as to maintain mechanical equilibrium of the sample in the acoustic field. The resultant deformation of the sample can be monitored with imaging diagnostics, as depicted in FIGS. 14A-E. FIG. 14A shows two samples simultaneously acoustically levitated and deformed in the apparatus shown in Example 1. FIGS. 13B-E depict a sequence of increasingly deformed samples resulting from a linear ramp amplitude modulation.

Material parameters may then be extracted from the unique series of deformed shapes measured using methods found in Tian Y, Holt R G, Apfel R E. A New Method for Measuring Liquid Surface-Tension with Acoustic Levitation. Review of Scientific Instruments 1995; 66:3349 and Tian Y, Holt R G, Apfel R E. Investigations of Liquid Surface Rheology of Surfactant Solutions by Droplet Shape Oscillations—Theory. Physics of Fluids 1995; 7:2938.

Example 9

Calibration

In order to calibrate the apparatus benchmark experiments are performed (using the above-described techniques) on well-characterized viscoelastic fluid materials. In one embodiment, a target material which is used as a calibration material is a polyurethane (American National Standards Institute, Inc. (1998.). *Method for preparation of a standard material for dynamic mechanical measurements*, ANSI S2.21-1998 (Acoustical Society of America; New York, N.Y.) (Whitten, C. W. and P. E. Greilich, *Thromboelastography: past, present, and future*. Anesthesiology, 2000. 92(5): p. 1223-5) whose rheological properties depend on the concentrations of its constituent prepolymer and chain extender (Chan, R. W. and M. L. Rodriguez, *A simple-shear rheometer for linear viscoelastic characterization of vocal fold tissues at phonatory frequencies*. Journal of the Acoustical Society of America, 2008. 124(2): p. 1207-1219). Composed of polytetramethylene ether glycol (molecular weight 2000), 4,4'-diphenylmethane-diisocyanate, and a chain extender blend of 2,2-dimethyl-1,3-propanediol and 1,4-butanediol, this ANSI standard material can be tailored to have elastic moduli on the order of kPa. In another embodiment, Xanthan gum is used due to storage, loss moduli and strain-rate dependence having been well studied and are known to vary with concentration of the Xanthan gum in water.

Experiments are performed with both types of forcing on samples of 5 fixed sizes (from the casting forms), varying the concentrations of ingredients in each mixture in order to achieve a range of elastic modulus and loss modulus spanning that expected from coagulating blood. The material properties (such as G' and G") of polyurethane and Xanthan gum gels are directly measured by a rheometer (e.g. TA Instruments AR2000 Rheometer). Results from this direct measurement provide validation as well as comparison to the data obtained from acoustic tweezing experiments.

Example 10

Analysis of Viscoelastic Fluid Drop in an Acoustic Levitator

The dynamics of a viscoelastic fluid drop are different in an acoustic levitator on Earth than that in microgravity. This is because the equilibrium drop shape ceases to be spherical (it is flattened) due to acoustic radiation pressure in the levitator. Using the analysis in Khismatullin D B, Nadim A. *Shape oscillations of a viscoelastic drop*. Phys Rev E Stat Nonlin Soft Matter Phys 2001; 63:061508 and including the acoustic radiation effect on drop shape and obtaining the relationships between material constants and shape oscillation parameters, similar to Eqs. (5) and (6), accomplishes necessary calculations. In this linear study, the deformation of a biological fluid sample is described by linear/linearized constitutive equations (e.g., linear Maxwell model, which is Eq. (4) without the retardation term). The governing equations for sample deformation will also include the continuity and momentum equations for an incompressible fluid:

$$\nabla \cdot v = 0, \rho \frac{\Delta v}{\Delta t} = -\nabla p + \nabla \cdot \tau + \rho g \quad (7)$$

and the kinematic and dynamic boundary conditions at the material surface:

$$v|_s = v_s, [p - p_o - n \cdot (\tau - \tau_o)]_s = \sigma(\nabla_s \cdot n)n. \quad (8)$$

Here p and τ are the pressure and shear stress tensor inside the material, $p_o$ and $\tau_o$ the pressure and shear stress tensor in the surrounding fluid, g the acceleration due to gravity, the symbol "s" means the material surface, $v_s$ is the velocity of the surface, n the outward unit normal vector to the surface, and ($\nabla_s \cdot n$) the surface curvature of the material, with $\nabla_s = \nabla - nn \cdot \nabla$ being the surface gradient operator. Other parameters are defined in the preliminary data section. Note that the relaxation time is the elasticity parameter in the Maxwell model. The difference between the inner and outer pressures, $p - p_o$, will have contributions from acoustic radiation and gravity, according to Tian, Y. R., R. G. Holt, and R. E. Apfel, *Deformation and Location of an Acoustically Levitated Liquid-Drop*. Journal of the Acoustical Society of America, 1993. 93(6): p. 3096-3104. These equations in the limit of small-amplitude oscillations are analyzed by using a spherical system of coordinates and expressing the surface profile of the fluid drop in terms of the Legendre polynomial. The analysis gives the characteristic equation for the frequency and damping rate of freely decaying shape oscillations of the viscoelastic fluid drop. This equation is analyzed in the high- and low-viscosity limits to obtain the formulas that relate material constants with oscillation parameters. These formulas are used to estimate material constants from the data on the frequency and damping rate of shape oscillations in step forcing experiments, as discussed above.

Material constants are then determined from experimental results obtained by swept-frequency forcing. Here, the sample undergoes forced oscillations and the pressure $p_o$ in the surrounding fluid contains the sinusoidal term which is estimated according to Tian, Y. R., R. G. Holt, and R. E. Apfel, *Deformation and Location of an Acoustically Levitated Liquid-Drop*. Journal of the Acoustical Society of America, 1993. 93(6): p. 3096-3104. Perturbation analysis is applied to the governing equations to derive the equation for forced shape oscillation and the expression for the amplitude-frequency response of the viscoelastic fluid drop. The viscoelastic parameters are determined from the best fit between the theoretical and experimental amplitude-frequency response curves. FIGS. 13A-B are examples of such fitting. In a preferred embodiment, fitting the amplitude-frequency response curves is used for determination of material viscoelasticity. In other embodiments, asymptotic formulas are used for determination of material viscoelasticity. The latter approach is simple and straightforward and is preferred in the situations when the high-viscosity approximation is valid.

To predict the nonlinear dynamics, a computational model for the deformation of a biological fluid sample under acoustic levitation is used. This model represents the axisymmetric version of the existing 3-D numerical code, discussed above, with an additional force term in the Navier-Stokes equations (acoustic radiation pressure). Fluid viscoelasticity is first described by the Giesekus equation. The models describing power law and yield stress fluids are then implemented. The computational model will use the Volume-of-Fluid (VOF) method for tracking the shape of the sample, i.e., the sample surface will be reconstructed from a concentration (or volume fraction) function that takes the value 1 in the first phase (interior of the sample) and the value 0 in the second phase (surrounding fluid). Note that in the VOF method, the boundary conditions at the sample surface [Eqs. (8)] cannot be applied directly and, therefore, all surface forces (including acoustic radiation pressure) should be included in the Navier-Stokes equations as body forces which act on the interior and exterior of the sample within a narrow transition region. The acoustic radiation force (force per unit volume) will be defined as $-(p-p_o)\nabla C$, where $\nabla C$ is the gradient of the concentration function. To infer the material constants from ramp forcing experiments, the length, breadth, and deformation index of the sample is compared between numerical and experimental shapes at different instants. The computational model will also be used to analyze weakly damped samples in swept-frequency sine forcing experiments.

The formulas derived from theoretical models are included in a data analysis software package written in FORTRAN programming language (the graphical user interface is written in C++). This software will allow the user to select which type of acoustic levitation/tweezing data he/she would like to analyze. It outputs dynamic changes in the viscoelastic properties of a coagulating blood sample in the form of a graph ("tweezograph", which will be similar to that of Sonoclot signature) and tabulated data.

In some embodiments, measurements can be performed at any range of temperatures desired, so long as the speed of sound in the host medium is tracked.

In some embodiments, sample sizes are no larger than 2 mm in diameter. In some embodiments, the sample size is smaller than a half-wavelength of the sound in the host medium.

In some embodiments, temporal parameters (frequency, relaxation) is limited by data acquisition rates. In some embodiments, the data acquisition rate is 1 MS/s, yielding for example a resolution of 1 microsecond.

In some embodiments, determination of size and shape is limited by imaging, but a resolution of 10 microns (and thus 1 part in 400 for a 4 mm diameter blood drop) is achievable with existing optics.

In some embodiments, oil is not used to coat biological samples. In some embodiments, where oil is used to slow evaporation and/or dehydration, any oil that is low viscosity and low surface tension may be used.

In some embodiments, a biological material is transferred to an acoustic levitator by a syringe.

In some embodiments, applying various embodiments of the disclosed techniques can capture subtle physical characteristics in viscoelastic materials that may well lead to new insights into the clot behavior in vivo. In some embodiments, the present device and methods comprise an ability to obtain results such as those plotted above for coagulating blood.

Example 11

Technique for Post Clotted Measurements

Figure 15A:
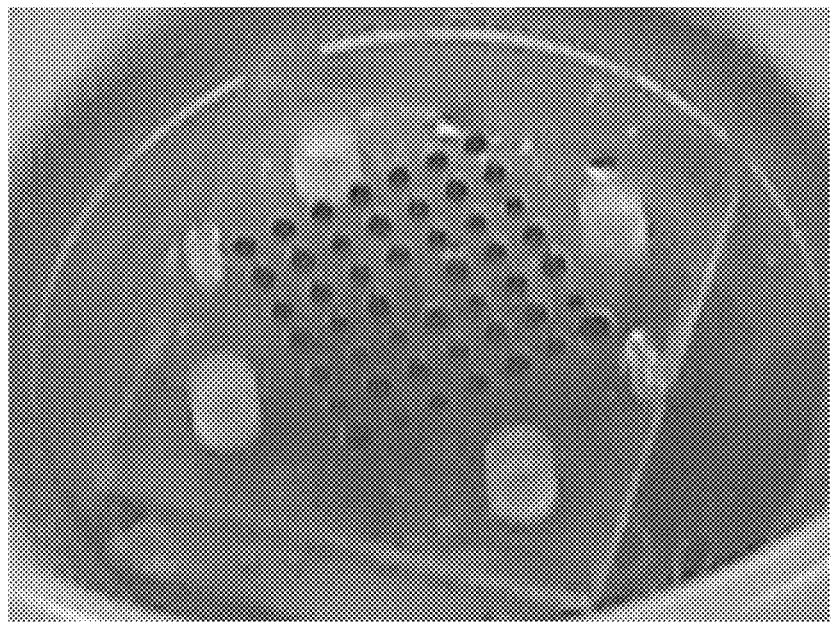
FIG. 15A depicts exemplary Bovine blood clots 2 mm in radius cast in a machined Plexiglas mold.
Figure 15B:
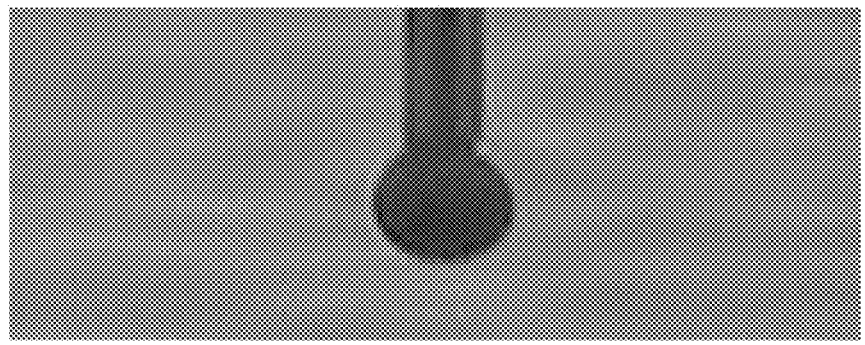
FIG. 15B depicts Bovine blood clot 2 mm in radius pendant on stainless steel flat-tipped needle in paraffin oil.
Figure 15C:
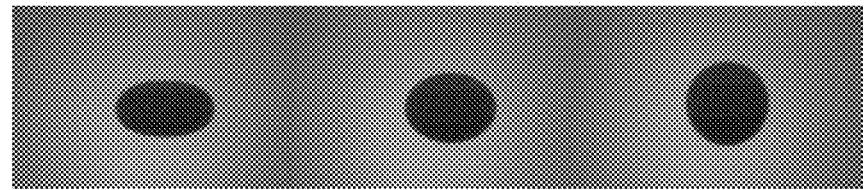
FIG. 15C depicts a series of images from a high speed movie of freshly calcified blood, prior to fully clotting, directly injected into a levitator, wherein the left and right images are the extrema of the shape oscillation, while the middle picture identifies the equilibrium.

FIG. 15A depicts exemplary Bovine blood clots 2 mm in radius cast in a machined Plexiglas mold. FIG. 15B depicts Bovine blood clot 2 mm in radius pendant on stainless steel flat-tipped needle in paraffin oil. FIG. 15C depicts a series of images from a high speed movie of freshly calcified blood directly injected into a levitator. The left and right images are the extrema of the shape oscillation, while the middle picture identifies the equilibrium. These images were taken before the blood is fully clotted. In this Example, small spherical bovine blood clots were successfully obtained via three techniques. FIGS. 15A-C depict an array of 2 mm radius spherical blood clots obtained in a Plexiglas mold with spherical cavities connected by small channels (FIG. 15A). About 5 of these clots were fully viable, with the rest having unclotted regions which compromised the spherical symmetry. These clots were transferred directly to the levitator using a pipette.

Under certain embodiments, it is a pendant drop technique for making a spherical clot has been successfully implemented, as is shown in FIG. 15B. The clotting blood was injected into an oil bath using a custom flat tip needle to provide nearly neutral buoyancy for sphericity, and provided an immiscible environment to contain the blood as it clotted. The trials performed yielded spheroidal clots of approximately 2 mm diameter every time. The clots were transferring to the levitator using the needle. The needle was cleaned prior to each use.

An embodiment of an acoustic levitation device (depicted in FIG. 4A-7) was used to levitate both preformed clots (using the techniques of FIGS. 15A-15B) and clotting blood. FIG. 15C shows 3 frames from a high-speed camera movie of an acoustically levitated clotting blood sample. As described above, the acoustic field was modulated to excite the quadrupole mode of drop oscillation. This family of results using blood and in vitro blood clots illustrates the viability and robustness of the disclosed invention.

Example 12

Analysis of Whole Blood

In some embodiments, whole blood samples are collected via venipuncture from healthy consenting volunteers. For experimental verification, blood samples are either used for experiments within 4 minutes of collection (to test the viscoelastic properties and coagulability of fresh whole blood) or citrated (10% sodium citrate and 90% blood) and kept on a tube rotator (e.g. Barnstead Thermolyne, Dubuque, Iowa) at room temperature for less than 24 hours (to test stored whole blood). In the latter case, blood samples are recalcified with 0.2 M calcium chloride immediately before perfoming experiments, as normally done in thromboelastography. Blood cell counts will be determined with a hematology analyzer (e.g. Medonic M-Series, Boule Diagnostics Int AB, Stockholm, Sweden).

Coagulation experiments in the acoustic tweezing system are done with fresh and stored whole blood. Here, blood collection tubing is attached to a Vacutainer tube containing blood. The open end of tubing will be connected to a tip needle. A small drop of blood is dripped from a needle into the space between the reflector and transducer of the acoustic levitator. These experiments provide the data necessary for the development of the "tweezograph" module of the data analysis software, which determines dynamic changes in the viscoelastic properties of coagulating blood.

In certain embodiments, the output data is in the tabulated form and as clot strength vs. time curve ("tweezograph"), similar to the output of the Sonoclot analyzer. The time evolution of the sample viscoelastic properties is directly obtained from fitting the amplitude-frequency response curve between the theoretical model (where material constants are functions of time) and the raw data from sample levitation with swept-frequency forcing. In some embodiments, sample levitation with step forcing at regular time intervals is used to produce the data to infer changes in blood viscoelasticity with coagulation.

In some embodiments, the rheometry system may be used to test the effects of procoagulants (such as kaolin, tissue factor, ellagic acid, and the like) on blood clotting, and anticoagulants (heparin, warfarin) and antiplatelet agents (e.g., cytochalasin D).

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as a basis for the claims and as a representative basis for teaching one skilled in the art to employ the present invention in any appropriate manner.

A number of embodiments have been described. Nevertheless it will be understood that various modifications may be made without departing from the spirit and scope of the invention. Accordingly, other embodiments are included as part of the invention and may be encompassed by the attached claims. Furthermore, the foregoing description of various embodiments does not necessarily imply exclusion. For example, "some" embodiments, "exemplary" embodiments, or "other" embodiments may include all or part of "some," "other," and "further" embodiments within the scope of this invention.

Although the disclosure has been described with reference to preferred embodiments, persons skilled in the art will recognize that changes may be made in form and detail without departing from the spirit and scope of the rheometry system, systems and methods.

What is claimed is:

1. A non-contact rheometry system for the elastic characterization of a single-drop biological sample, the system comprising:
   a. an acoustic levitator comprising:
      i. an acoustic reflector;
      ii. a transducer;
      iii. a light source; and
      iv. a camera configured to record deformation of the biological sample including its quasistatic deformation;
   b. at least one function generator; and
   c. a data processing system comprising a computer in operational communication with the function generator and acoustic levitator,
   wherein:
      i. the levitator is constructed and arranged to levitate the biological sample at frequencies of between 28 kHz and about 40 kHz;
      ii. the at least one function generator is configured to induce quasistatic deformation of the biological sample,
      iii. the data processing system is configured to analyze, based on aspect ratio vs. location data, at least one mechanical elastic property of the biological sample undergoing quasistatic deformation as recorded by the camera, and
      iv. the biological sample is selected from the group consisting of whole blood, blood plasma, biological polymer solution, biological hydrogel clotting blood, and blood clots.

2. The non-contact rheometry system of claim 1, wherein the function generator provides a carrier frequency of at least 10 kHz.

3. The non-contact rheometry system of claim 1, further comprising a sample introduction device.

4. The non-contact rheometry system of claim 3, wherein the sample introduction device is selected from the group consisting of a syringe with a needle and an automatic pipette.

5. The non-contact rheometry system of claim 1, wherein at least one function generator is configured to provide amplitude modulation.

6. The non-contact rheometry system of claim 5, wherein the function generator providing amplitude modulation is configured for step forcing.

7. The non-contact rheometry system of claim 6, wherein the acoustic pressure amplitude is increased or decreased with a rise time of 1 ms.

8. The non-contact rheometry system of claim 5, wherein the function generator providing amplitude modulation utilizes swept-frequency sine forcing.

9. The non-contact rheometry system of claim 1, wherein the at least one elastic property comprises relaxation time of the biological sample.

10. A non-contact mechanical rheometry system for the rheological measurement of a single drop of blood, the system comprising:
    a. an acoustic levitator;
    b. a camera configured to record deformation of the blood including its quasistatic deformation;
    c. at least one function generator configured to generate a carrier wave; and
    d. a data processing system comprising a computer in operational communication with the function generator and acoustic levitator;
    wherein the acoustic levitator is configured to levitate the blood at a frequency of 28 kHz to about 40 kHz and induce quasistatic deformation in the blood and the data processing system is configured to measure and analyze the elastic properties of the blood over time based on aspect ratio vs. location data.

11. The non-contact rheometry system of claim 10, further comprising a transducer.

12. The non-contact rheometry system of claim 11, wherein the amplitude of carrier wave is modulated by a sine wave with frequency of at least 10 kHz.

13. The non-contact rheometry system of claim 12, wherein the function generator modulates amplitude using ramp forcing.

14. A non-contact method of measuring the rheological properties of single drops of clotting blood, the method comprising:
    a. transferring the clotting blood into an acoustic levitator;
    b. modulating the amplitude of pressure within the acoustic levitator;
    c. levitating the clotting blood using acoustic radiation at a frequency of between 28 kHz and about 40 kHz;
    d. taking measurements of the quasistatic deformation of the clotting blood; and
    e. analyzing the quasistatic deformation of the clotting blood to determine mechanical elastic properties based on aspect ratio vs. location data.

15. The non-contact method of claim 14, wherein the acoustic levitator further comprises:
    a. an acoustic reflector;
    b. a transducer;
    c. a light source;
    d. a photodiode;
    e. a camera;
    f. at least one function generator configured to generate a carrier wave; and
    g. a data processing system comprising a computer in operational communication with the function generator and acoustic levitator.

16. The non-contact method of claim 14, comprising taking measurements of oscillatory and quasistatic deformation of the clotting blood in sequence.

* * * * *